(12) United States Patent
Chari et al.

(10) Patent No.: US 6,596,757 B1
(45) Date of Patent: Jul. 22, 2003

(54) CYTOTOXIC AGENTS COMPRISING POLYETHYLENE GLYCOL-CONTAINING TAXANES AND THEIR THERAPEUTIC USE

(75) Inventors: Ravi V. J. Chari, Newton, MA (US); Michael Louis Miller, Somerville, MA (US)

(73) Assignee: Immunogen Inc., Cambridge, MA (US)

( * ) Notice: Subject to any disclaimer, the term of this patent is extended or adjusted under 35 U.S.C. 154(b) by 0 days.

(21) Appl. No.: 10/144,042

(22) Filed: May 14, 2002

(51) Int. Cl.[7] ............... A61K 31/337; C07D 305/14

(52) U.S. Cl. ............ 514/449; 549/510; 549/511; 528/421

(58) Field of Search ............ 514/449; 549/510, 549/511; 528/421

(56) References Cited

U.S. PATENT DOCUMENTS 5,648,506 A    7/1997    Desai et al.
5,824,701 A  * 10/1998    Greenwald et al. ......... 514/449

* cited by examiner

*Primary Examiner*—Ba K. Trinh
(74) *Attorney, Agent, or Firm*—Sughrue Mion, PLLC

(57) ABSTRACT

A cytotoxic agent comprising one or more polyethylene glycol-containing taxanes linked to a cell binding agent. A therapeutic composition for killing selected cell populations comprising: (A) a cytotoxic amount of one or more polyethylene glycol-containing taxanes covalently bonded to a cell binding agent through a linking group, and (B) a pharmaceutically acceptable carrier, diluent or excipient. A method for killing selected cell populations comprising contacting target cells or tissue containing target cells with an effective amount of a cytotoxic agent comprising one or more polyethylene glycol-containing taxanes linked to a cell binding agent.

48 Claims, 11 Drawing Sheets

| Compound | $R_1$ | $R_2$ | $R_3$ | $R_4$ | $R_5$ |
|---|---|---|---|---|---|
| Paclitaxel (Taxol) | -H | -COCH$_3$ | -C$_6$H$_5$ | -C$_6$H$_5$ | H |
| Docetaxel (Taxotere) | -H | -H | -C$_6$H$_5$ | -OC(CH$_3$)$_3$ | H |
| More Potent Taxanes | -OCH$_3$ | -COCH$_2$CH$_3$ | -CH=C(CH$_3$)$_2$ | -OC(CH$_3$)$_3$ | H |
| | -F | -COCH$_2$CH$_3$ | -CH=C(CH$_3$)$_2$ | -OC(CH$_3$)$_3$ | H |
| | -Cl | -COCH$_2$CH$_3$ | -CH=C(CH$_3$)$_2$ | -OC(CH$_3$)$_3$ | H |

Figure 2

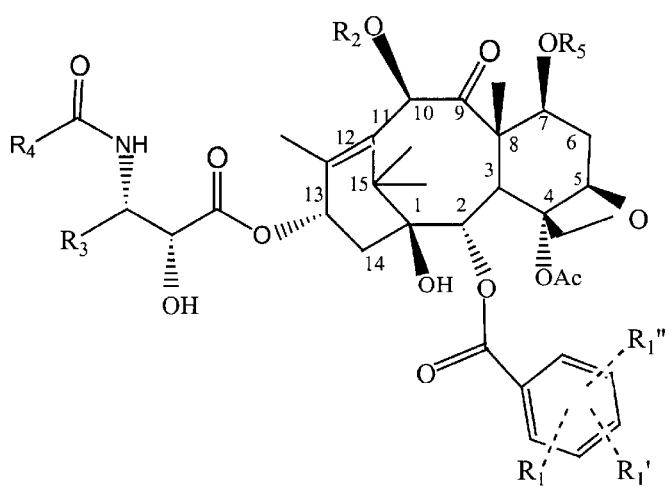

| | $R_1$ | $R_{1'}$ | $R_2$ | $R_3$ | $R_4$ | $R_5$ |
|---|---|---|---|---|---|---|
| 1 | -OMe | -OMe | -COCH$_2$CH$_2$(OCH$_2$CH$_2$)$_n$SH<br>-CONHCH$_2$CH$_2$(OCH$_2$CH$_2$)$_n$SH<br>-CH$_2$CH$_2$(OCH$_2$CH$_2$)$_n$SH | -CH=C(CH$_3$)$_2$<br>-CH$_2$CH(CH$_3$)$_2$<br>-C$_6$H$_5$ | -OC(CH$_3$)$_3$<br>or -C$_6$H$_5$ | -H<br>-COCH$_2$CH$_3$<br>-CH$_2$CH$_3$, or<br>-CONHCH$_2$CH$_3$ |
| 2 | -OMe | -OMe | -H<br>-COCH$_2$CH$_3$<br>-CH$_2$CH$_3$, or<br>-CONHCH$_2$CH$_3$ | -CH=C(CH$_3$)$_2$<br>-CH$_2$CH(CH$_3$)$_2$<br>-C$_6$H$_5$ | -OC(CH$_3$)$_3$<br>or -C$_6$H$_5$ | -COCH$_2$CH$_2$(OCH$_2$CH$_2$)$_n$SH<br>-CONHCH$_2$CH$_2$(OCH$_2$CH$_2$)$_n$SH<br>-CH$_2$CH$_2$(OCH$_2$CH$_2$)$_n$SH |

Figure 3
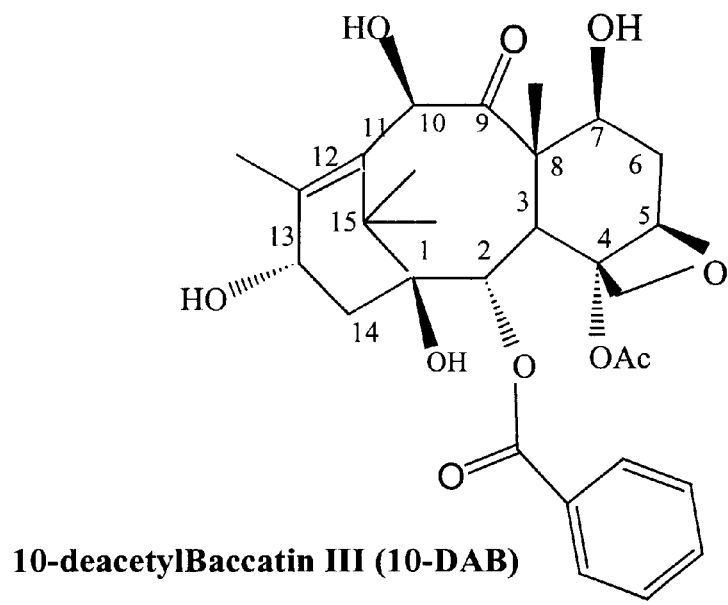
10-deacetylBaccatin III (10-DAB)
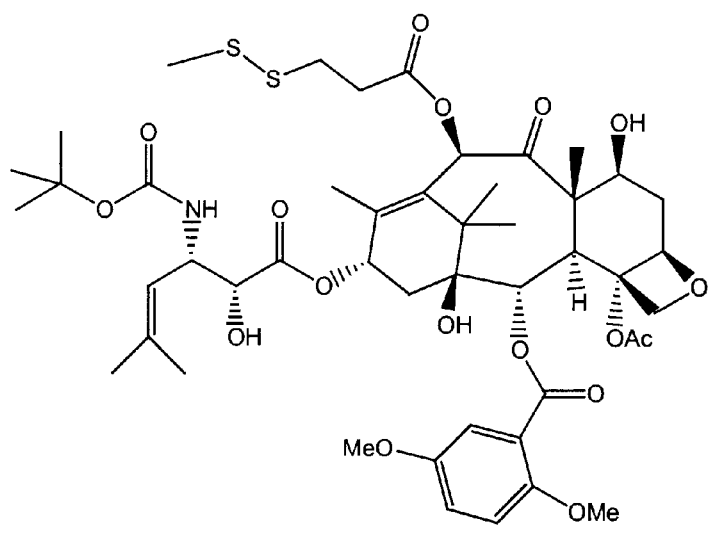
Parent Taxoid 1

P = protecting group such as: Ph₃C-, t-Bu

Figure 9    *In vitro* Cytotoxicity of PEG-Taxoid 17 towards MCF-7 cells
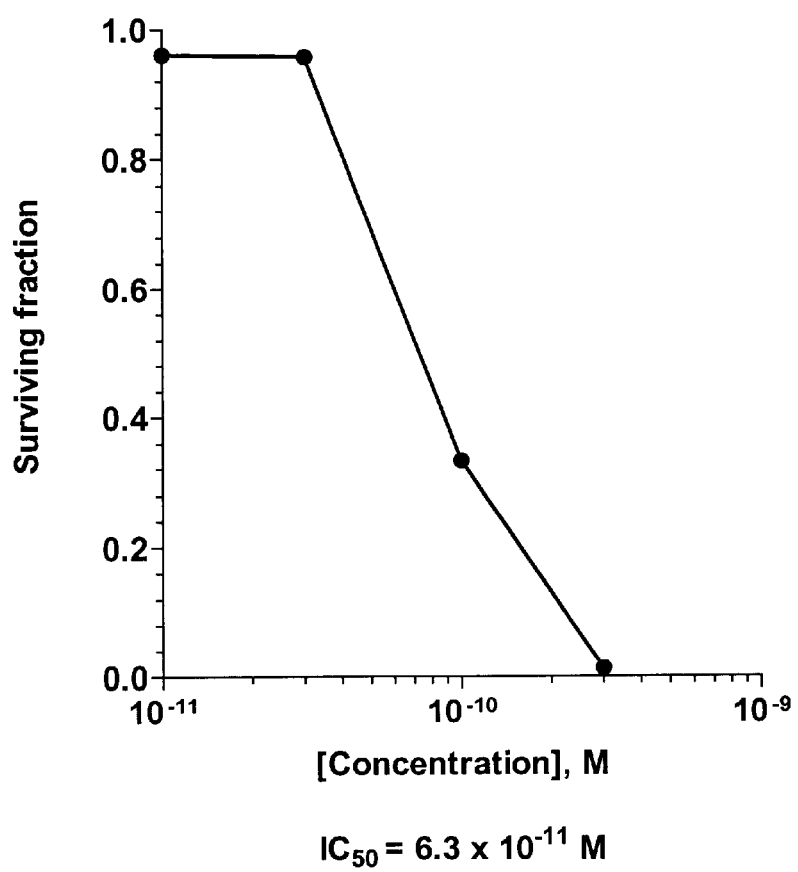

Figure 10   Comparison of the *In vitro* Cytotoxicity of PEG-Taxoid 17 and the Parent Non-PEGylated Taxoid 1 towards A-431 Cells.
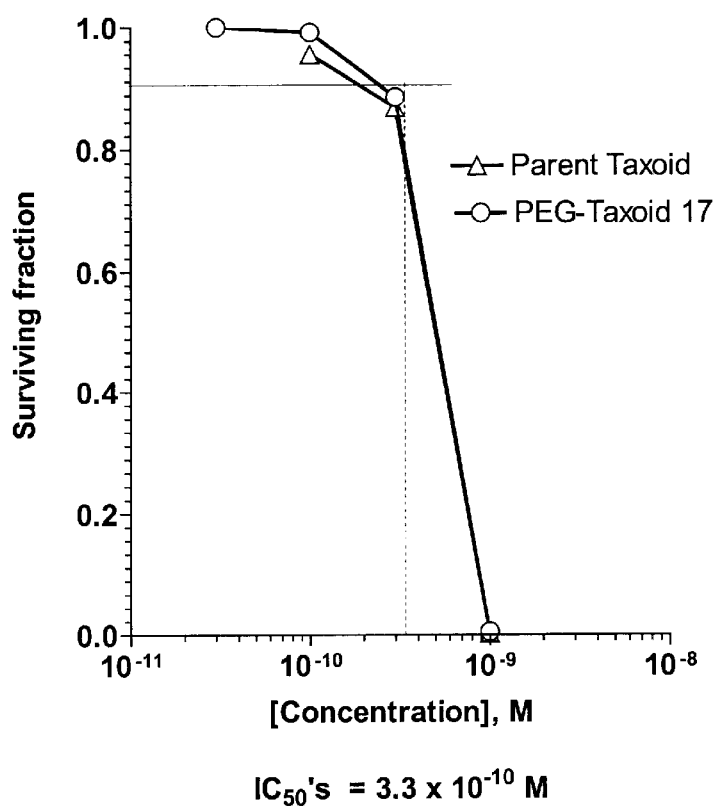
$IC_{50}$'s = 3.3 x $10^{-10}$ M Figure 11 *In Vitro* Cytotoxicity of PEG-Taxoid 20 towards MCF-7 Cells
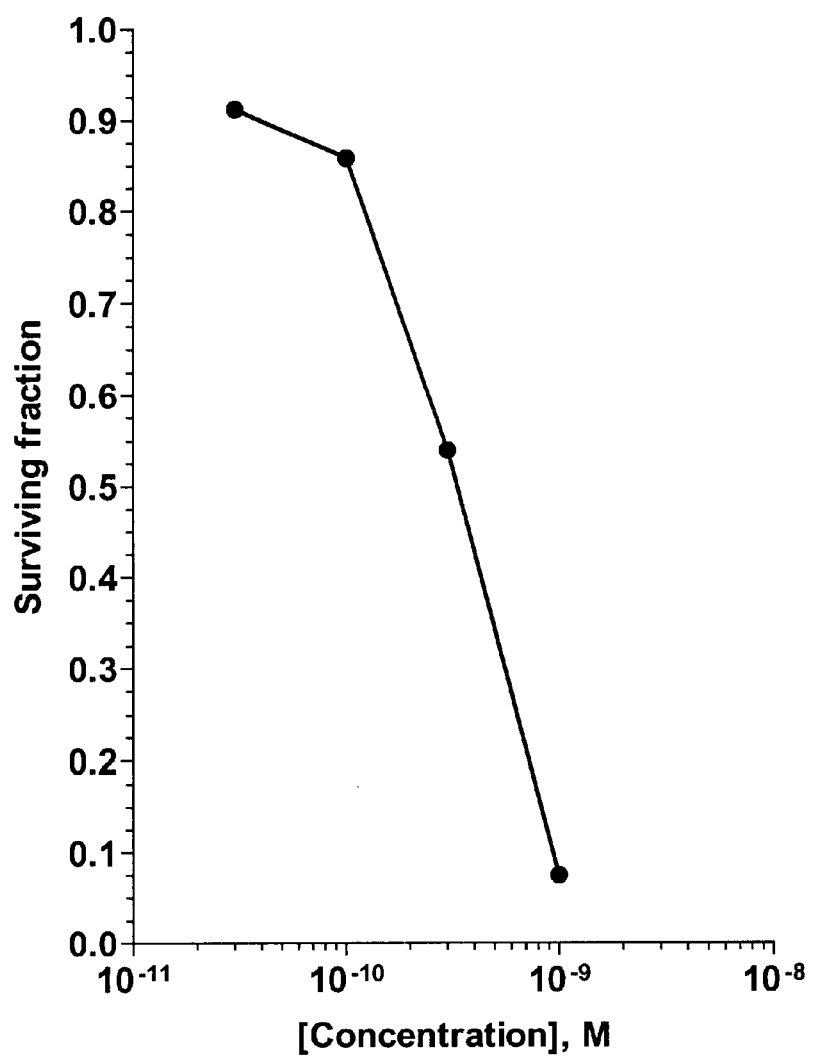
$IC_{50} = 3.2 \times 10^{-10} M$

CYTOTOXIC AGENTS COMPRISING POLYETHYLENE GLYCOL-CONTAINING TAXANES AND THEIR THERAPEUTIC USE

FIELD OF THE INVENTION

The present invention relates to novel cytotoxic agents with enhanced water solubility and their therapeutic uses. More specifically, the invention relates to novel cytotoxic agents that are taxanes which comprise both a polyethylene glycol moiety that enhances water solubility and a means of chemical linkage to a cell binding agent. These taxanes can be chemically linked to cell binding agents to provide therapeutics that are delivered to specific cell populations in a targeted manner.

BACKGROUND OF THE INVENTION

Many reports have appeared which are directed to the tageting of tumor cells with monoclonal antibody-drug conjugates (Sela et al, in Immunoconjugates, pp. 189–216 (C. Vogel, ed. 1987); Ghose et al, in Targeted Drugs, pp. 1–22 (E. Goldberg, ed. 1983); Diener et al, in Antibody Mediated Delivery Systems, pp. 1–23 (J. Rodwell, ed. 1988); Pietersz et al, in Antibody Mediated Delivery Systems, pp. 25–53 (J. Rodwell, ed. 1988); Bumol et al, in Antibody Mediated Delivery Systems, pp. 55–79 (J. Rodwell, ed. 1988), G. A. Pietersz and K. Krauer, 2 J. Drug Targeting, 183–215 (1994), R. V. J. Chari, 31 Adv. Drug Delivery Revs., 89–104 (1998); W. A. Blattler and R. V. J. Chari, in Anticancer Agents, Frontiers in Cancer Chemotherapy, 317–338, ACS Symposium Series 796, I. Ojima et al eds, American Chemical Society 2001). Cytotoxic drugs such as methotrexate, daunorubicin, doxorubicin, vincristine, vinblastine, melphalan, mitomycin C, chlorambucil, calicheamicin and maytansinoids have been conjugated to a variety of murine monoclonal antibodies. In some cases, the drug molecules were linked to the antibody molecules through an intermediary carrier molecule such as serum albumin (Garnett et al, 46 Cancer Res. 2407–2412 (1986); Ohkawa et al, 23 Cancer Immunol. Immunother. 81–86 (1986); Endo et al, 47 Cancer Res. 1076–1080 (1980)), dextran (Hurwitz et al, 2 Appl. Biochem. 25–35 (1980); Manabi et al, 34 Biochem. Pharmacol. 289–291 (1985); Dillman et al, 46 Cancer Res. 4886–4891 (1986); Shoval et al, 85 Proc. Natl. Acad. Sci. U.S.A. 8276–8280 (1988)), or polyglutamic acid (Tsukada et al, 73 J. Natl. Canc. Inst. 721–729 (1984); Kato et al, 27 J. Med. Chem. 1602–1607 (1984); Tsukada et al, 52 Br. J. Cancer 111–116 (1985).

A wide array of linkers is now available for the preparation of such immunoconjugates, including both cleavable and non-cleavable linkers. In vitro cytotoxicity tests, however, have revealed that antibody-drug conjugates rarely achieve the same cytotoxic potency as the free unconjugated drugs. This suggested that mechanisms by which drug molecules are released from conjugated antibodies are very inefficient. Early work in the area of immunotoxin conjugates showed that conjugates formed via disulfide bridges between monoclonal antibodies and catalytically active protein toxins were more cytotoxic than conjugates containing other linkers. See, Lambert et al, 260 *J. Biol. Chem.* 12035–12041 (1985); Lambert et al, in Immunotoxins 175–209 (A. Frankel, ed. 1988); Ghetie et al, 48 *Cancer Res.* 2610–2617 (1988). This improved cytotoxicity was attributed to the high intracellular concentration of reduced glutathione contributing to the efficient cleavage of the disulfide bond between the antibody molecule and the toxin. Maytansinoids and calicheamicin are the first examples of highly cytotoxic drugs that have been linked to monoclonal antibodies via disulfide bonds. Antibody conjugates of these drugs have been shown to possess high potency in vitro and exceptional antitumor activity in human tumor xenograft models in mice (R. V, J. Chari et al., 52 *Cancer Res.*, 127–131 (1992), C. Liu et al., 93, *Proc. Natl. Acad. Sci.*, 8618–8623 (1996), L. M. Hinman et al., 53, *Cancer Res.*, 3536–3542 (1993), P. R. Hamann et al, 13, *BioConjugate Chem.*, 40–46 (2002)).

One reason for the lack of disulfide linked antibody-drug conjugates is the unavailability of cytotoxic drugs possessing a sulfur atom containing moiety that can be readily used to link the drug to an antibody via a disulfide bridge. Furthermore, chemical modification of existing drugs is difficult without diminishing their cytotoxic potential.

In spite of the above described difficulties, useful cytotoxic agents comprising cell binding moieties and the group of cytotoxic drugs known as maytansinoids have been reported (U.S. Pat. No. 5,208,020, U.S. Pat. No. 5,416,064, and R. V. J. Chari, 31 *Advanced Drug Delivery Reviews* 89–104 (1998)). Similarly, useful cytotoxic agents comprising cell binding moieties and analogues and derivatives of the potent antitumor antibotic CC-1065 have also been reported (U.S. Pat. No. 5,475,092 and U.S. Pat. No. 5,585,499).

Paclitaxel (Taxol®), a cytotoxic natural product, and docetaxel (Taxotere®), a semi-synthetic derivative (See FIG. 1), are widely used in the treatment of cancer. These compounds belong to the family of compounds called taxanes. Taxanes are mitotic spindle poisons that inhibit the depolymerization of tubulin, resulting in an increase in the rate of microtubule assembly and cell death. While docetaxel and paclitaxel are useful agents in the treatment of cancer, their antitumor activity is limited because of their non-specific toxicity towards normal cells.

Further, compounds like paclitaxel and docetaxel themselves are not sufficiently potent to be used in conjugates of cell binding agents. Recently, a few new taxanes with greater potency than either docetaxel or paclitaxel have been prepared (FIG. 1). In addition, these taxanes bear a suitable functionality that allows linkage via a cleavable bond to cell binding agents (U.S. Pat. Nos. 6,340,701 and 6,372,738). However, these taxanes display poor aqueous solubility. Thus linkage to cell binding agents, which are typically only soluble in water, necessitates the use of a high percentage of an organic co-solvent which could lead to damage of the cell binding agent. Thus, conjugation reactions with cell-binding agents currently have to be performed in extremely dilute aqueous solutions.

One approach commonly used to enhance the aqueous solubility of poorly soluble drugs such as paclitaxel is to convert them into prodrugs by incorporating a polyethylene glycol spacer of varying chain lengths, in a process often called PEGylation. These prodrugs are inactive or poorly active in vitro, and have to rely on in vivo enzymatic cleavage of the polyethylene glycol group to be activated. Such in vivo cleavage mechanisms are inefficient resulting in poor conversion into active drug. In addition, these PEGylated-taxanes do not have a linking group that allows for conjugation to cell binding agents (U.S. Pat. Nos. 5,614,549; 5,648,506; 5,880,131; 5,824,701; R. B. Greenwald et al., 60, *J. Org. Chem.*, 331–336 (1995), R. B. Greenwald et al., 39, *J. Med. Chem.*, 424–431 (1996), A. E. Matthew et al., 35, *J. Med. Chem.*, 145–151 (1992)).

Accordingly, a method of providing taxanes that contain a polyethylene glycol moiety that confers enhanced aqueous solubility, while preserving cytotoxic potency, without the need for additional in vivo activation is required. These PEGylated taxanes must also possess a linking group that allows for linkage with cell binding agents. Thus, a method of using these taxanes for treating diseases wherein their side effects are reduced without compromising their cytotoxicity is greatly needed.

SUMMARY OF THE INVENTION

One object of the present invention is to provide novel taxanes that incorporate a polyethylene glycol moiety that confers enhanced aqueous solubility.

Another object of the present invention is to provide polyethylene glycol-containing taxanes that are highly cytotoxic in vitro and that can still be effectively used in the treatment of many diseases.

These and other objects have been achieved by providing a taxane comprising a polyethylene glycol-containing linking group at C-7 or C-10, the linking group being capable of linking the taxanes to a cell binding agent or other chemical moiety.

The invention also provides a cytotoxic agent comprising one or more taxanes linked to a cell binding agent through a polyethylene glycol-containing linking group at C-7 or C-10 of at least one of the taxanes.

The present invention also provides a therapeutic composition comprising an effective amount of a cytotoxic agent comprising one or more taxanes linked to a cell binding agent through a polyethylene glycol-containing linking group at C-7 or C-10 of at least one of the taxanes; and (B) A pharmaceutically acceptable carrier, diluent, or excipient.

The present invention also provides a method of killing selected cell populations comprising contacting the target cells or tissue containing target cells with a cytotoxic amount of the above-described cytotoxic agent.

BRIEF DESCRIPTION OF THE DRAWINGS

FIG. 2 is a chemical formula that represents structures of some of the polyethylene glycol-containing taxanes according to the present invention.

FIG. 3 shows the structure of 10-deacetylbaccatin III, which is the starting material for preparing the taxanes of the present invention and the structure of the parent taxoid.

FIGS. 9, 10 and 11 show the in vitro cytotoxicity of polyethylene glycol-containing taxanes according to the present invention.

DETAILED DESCRIPTION OF THE INVENTION

Figure 1:
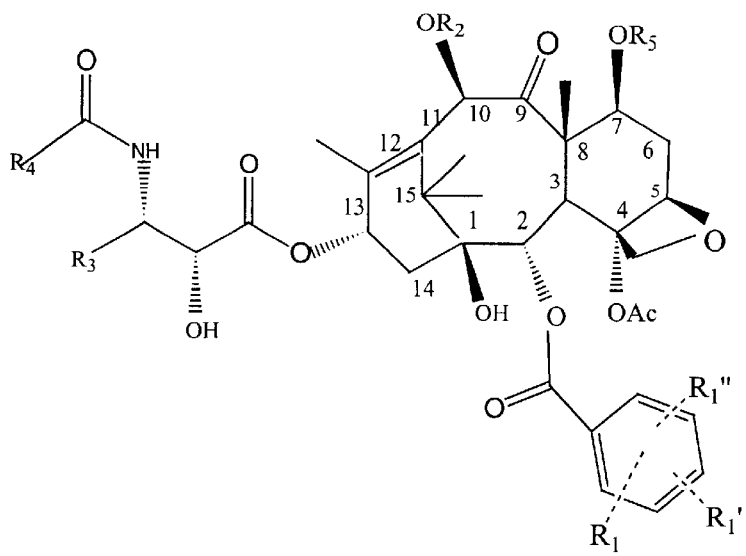
FIG. 1 is a chemical formula that represents structures of various taxanes, including some of the more potent taxanes described in U.S. Pat. Nos. 6,340,701 and 6,372,738.

This invention is based on the synthesis of novel taxanes that retain high cytotoxicity and that can be linked effectively to cell binding agents. It has previously been shown that the linkage of highly cytotoxic drugs to antibodies using a cleavable link, such as a disulfide bond, ensures the release of fully active drug inside the cell, and such conjugates are cytotoxic in an antigen specific manner (R. V, J. Chari et al, 52 Cancer Res. 127–131 (1992); U.S. Pat. No. 5,475,092; and U.S. Pat. Nos. 5,416,064, 6,340,701 and 6,372,738). However, the art reveals that it is extremely difficult to modify drugs to improve their aqueous solubility without eliminating their cytotoxic potential. The disclosed invention overcomes this problem by modifying the disclosed taxanes with chemical moieties, and especially ones containing polyethylene glycol groups, to which appropriate cell binding agents can be linked. As a result, the disclosed novel taxanes have greater water solubility along with higher cytotoxic potency than that of known taxanes. The cell binding agent-taxane conjugates permit the full measure of the cytotoxic action of the taxanes to be applied in a targeted fashion against unwanted cells only, therefore, avoiding side effects due to damage to non-targeted healthy cells. This invention facilitates the linkage of taxanes to cell binding agents in aqueous media which had previously been difficult. Thus, the invention provides useful agents for the elimination of diseased or abnormal cells that are to be killed, lysed, or destroyed, such as tumor cells (particularly solid tumor cells), virus infected cells, microorganism infected cells, parasite infected cells, autoimmune cells (cells that produce autoantibodies), activated cells (those involved in graft rejection or graft vs. host disease), or any other type of diseased or abnormal cells, while exhibiting a minimum of side effects.

The cytotoxic agent according to the present invention comprises one or more polyethylene glycol-containing taxanes linked to a cell binding agent via a linking group. The linking group is part of a chemical moiety that is covalently bound to a taxane through conventional methods. In a preferred embodiment, the chemical moiety can be covalently bound to the taxane via a disulfide linkage.

The taxanes useful in the present invention may have the formula (I) shown below:

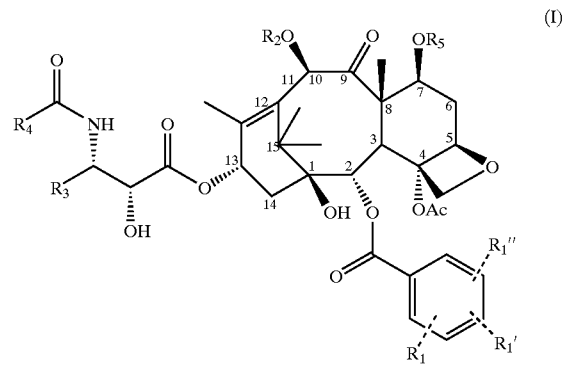

(I)

The novel taxanes of the invention can be divided into two embodiments, (1) and (2) based on the position of the PEG substituent bearing a linking group. Examples of the two embodiments are shown in FIG. 2.

In both embodiments, $R_1$ can be H, an electron withdrawing group, such as F, $NO_2$, CN, Cl, $CHF_2$, or $CF_3$ or an electron donating group such as —$OCH_3$, —$OCH_2CH_3$, —$NR_6R_7$, —$OR_8$, and $R_1'$ and $R_1''$ are the same or different and can be H, an electron withdrawing group, or an electron donating group.

$R_6$ and $R_7$ are the same or different and each can be H, linear, branched, or cyclic alkyl groups having 1 to 10 carbon atoms, or simple or substituted aryl having 1 to 10 carbon atoms. $R_8$ can be linear, branched or cyclic alkyl having 1 to 10 carbon atoms.

Preferably, $R_6$ and $R_7$ are each H or are alkyl or aryl groups having 1 to 4 carbon atoms. Examples of preferred —$NR_6R_7$ groups include dimethyl amino, diethyl amino, dipropyl amino, and dibutyl amino, where the butyl moiety is any of primary, secondary, tertiary or isobutyl. $R_1$ is preferably OMe, OEt, Cl, F, $NO_2$, or $CF_3$.

Preferably, $R_1$ is in the meta position and $R_1'$ is OMe, and $R_1''$ is H.

In both embodiments, $R_3$ can be aryl or is linear, branched or cyclic alkyl having 1 to 10 carbon atoms, preferably —$CH_2CH(CH_3)_2$, —$CH=C(CH_3)_2$ or —$C_6H_5$.

In both embodiments, $R_4$ can be —$OC(CH_3)_3$ or —$C_6H_5$.

In embodiment (1) $R_2$ is a PEG-containing linking group and $R_5$ can be H, a heterocyclic, a linear, branched, or cyclic ester or ether having from 1 to 10 carbon atoms or a carbamate of the formula —$CNR_{10}R_{11}$, wherein $R_{10}$ and $R_{11}$ are the same or different and can be H, linear, branched, or cyclic alkyl having 1 to 10 atoms or simple or substituted aryl. For esters, preferred examples include —$COCH_3$ —$COCH_2CH_3$ and —$COCH_2CH_2CH_3$. For carbamates, preferred examples include —$CONHCH_2CH_3$, —$CONHCH_2CH_3$, —CO-morpholino, —CO-piperazino, —CO-piperidino, or —CO-N-methylpiperazino.

In embodiment (2), $R_5$ is a PEG-containing linking group and $R_2$ can be H or can have the same definition as above for $R_5$ for embodiment (1)

Suitable linking groups are well known in the art and include disulfide groups, thioether groups, acid labile groups, photolabile groups, peptidase labile groups and esterase labile groups. Preferred are disulfide groups and thioether groups.

When the linking group is a thiol- or disulfide-containing group, the side chain carrying the thiol or disulfide group can be linear or branched, aromatic or heterocyclic. The taxane is linked to the polyethylene glycol through the hydroxyl group on the taxane. The hydroxyl group is used to form, for example, an ether, ester, or carbamate to link to one end of the polyethylene glycol. The moiety that contains the thiol- or disulfide group is linked to the other end of the polyethylene glycol. This linking moiety will contain, for example, an ether, ester, amide or carbamate. One of ordinary skill in the art can readily identify suitable side chains. Specific examples of the thiol- or disulfide-containing side chains include:

—$(CR_{13}R_{14})_l(CH_2)_m(CR_{13}R_{14})_l(OCH_2CH_2)_nO$ $(CR_{13}R_{14})_l(CH_2)_m(CR_{13}R_{14})_l(SZ$, —$CO(CR_{13}R_{14})_l$ $(CH_2)_mCR_{13}R_{14})_l(OCH_2CH_2)_nO(CR_{13}R_{14})_l(CH_2)_m$ $(CR_{13}R_{14})_lSZ$, —$CONR_{12}(CR_{13}R_{14})_l(CH_2)_m$ $(CR_{13}R_{14})_l(OCH_2CH_2)_nO(CR_{13}R_{14})_l(CH_2)_m$ $(CR_{13}R_{14})_lSZ$, —$(CR_{13}R_{14})_l(CH_2)_m(CR_{13}R_{14})_l$ $(OCH_2CH_2)_nOCO(CR_{13}R_{14})_l(CH_2)_m(CR_{13}R_{14})_lSZ$, —$(CR_{13}R_{14})_l(CH_2)_m(CR_{13}R_{14})_l(OCH_2CH_2)_nNR_{12}CO$ $(CR_{13}R_{14})_l(CH_{2m(CR13}R_{14})_lSZ$, —$(CR_{13}R_{14})_l(CH_2)_m$ $(CR_{13}R_{14})_l(OCH_2CH_2)_nOCONR_{12}(CR_{13}R_{14})_l(CH_2)_m$ $(CR_{13}R_{14})_lSZ$, —$CO(CR_{13}R_{14})_l(CH_2)_m(CR_{13}R_{14})_l$ $(OCH_2CH_2)_nOCO(CR_{13}R_{14})_l(CH_2)_m(CR_{13}R_{14})_lSZ$, —$CO(CR_{13}R_{14})_l(CH_2)_m(CR_{13}R_{14})_l(OCH_2$ $CH_2)_nNR_{12}CO(CR_{13}R_{14})_l(CH_2)_m(CR_{13}R_{14})_lSZ$, —$CO$ $(CR_{13}R_{14})_l(CH_2)_m(CR_{13}R_{14})_l(OCH_2CH_2)_nOCONR_{12}$ $(CR_{13}R_{14})_l(CH_2)_m(CR_{13}R_{14})_lSZ$, —$CONR_{12}$ $(CR_{13}R_{14})_l(CH_2)_m(CR_{13}R_{14})_l(OCH_2CH_2)_nOCO$ $(CR_{13}R_{14})_l(CH_2)_m(CR_{13}R_{14})_lSZ$, —$CONR_{12}$ $(CR_{13}R_{14})_l(CH_2)_m(CR_{13}R_{14})_l(OCH_2CH_2)_nNR_{12}CO$ $(CR_{13}R_{14})_l(CH_2)_m(CR_{13}R_{14})_lSZ$, —$CONR_{12}$ $(CR_{13}R_{14})_l(CH_2)_m(CR_{13}R_{14})_l(OCH_2CH_2)_nOCONR_{12}$ $(CR_{13}R_{14})_l(CH_2)_m$—$CR_{13}R_{14})_lSZ$, —CO-morpholino-$X(OCH_2CH_2)_nSZ$, —CO-piperazino-$X(OCH_2CH_2)_n$ $SZ$, —CO-piperidino-$X(OCH_2CH_2)_nSZ$, and —CO-N-methylpiperazino-$X(OCH_2CH_2)_nSZ$, wherein Z is H or SR, X is a linear alkyl or branched alkyl having 1–10 carbon atoms, R and $R_{12}$ are the same or different and represent linear alkyl, branched alkyl or cyclic alkyl having 1 to 10 carbon atoms, or simple or substituted aryl or heterocyclic, and $R_{12}$ can in addition be H, $R_{13}$ and $R_{14}$ are same or different and represent H or linear alkyl, branched alkyl or cyclic alkyl having 1 to 10 carbon atoms, or simple or substituted aryl, l is 0 or an integer from 1 to 10, m is an integer of 1 to 10, and n is 2 to 1000.

Examples of linear alkyls include methyl, ethyl, propyl, butyl, pentyl and hexyl.

Examples of branched alkyls include isopropyl, isobutyl, sec-butyl, tert-butyl, isopentyl and 1-ethyl-propyl.

Examples of cyclic alkyls include cyclopropyl, cyclobutyl, cyclopentyl and cyclohexyl.

Examples of simple aryls include phenyl and naphthyl.

Examples of substituted aryls include aryls such as those described above substituted with alkyl groups, with halogens, such as Cl, Br, F, nitro groups, amino groups, sulfonic acid groups, carboxylic acid groups, hydroxy groups or alkoxy groups.

Examples of heterocyclics are compounds wherein the heteroatoms are selected from O, N, and S, and include morpholino, piperidino, piperazino, N-methylpiperazino, pyrrollyl, pyridyl, furyl and thiophene.

The taxanes of the present invention that have a PEG-containing thiol- or disulfide-containing substituent are in themselves novel.

The taxanes that have a PEG-containing thiol or disulfide-containing substituent can be synthesized according to known methods. The starting material for the synthesis is the commercially available 10-deacetylbaccatin III, shown in FIG. 3. The chemistry to introduce various substituents is described in several publications (Ojima et al, *J. Med. Chem.*39, 3889–3896, (1996), Ojima et al., 40 *J. Med. Chem.* 267–278 (1997); I. Ojima et al., 96 *Proc. Natl. Acad. Sci.*, 4256–4261 (1999); I. Ojima et al., U.S. Pat. No. 5,475,011 and U.S. Pat. No. 5,811,452).

The substituent $R_1$ on the phenyl ring and the position of the substituent $R_1$ can be varied until a compound of the desired toxicity is obtained. Furthermore, the degree of substitution on the phenyl ring can be varied to achieve a desired toxicity. That is, the phenyl ring can have one or more substituents (e.g., mono-, di-, or tri-substitution of the phenyl ring) which provide another means for achieving a desired toxicity. High cytotoxicity is defined as exhibiting a toxicity having an $IC_{50}$ in the range of $1\times10^{-12}$ to $3\times10^{-9}$ M, when measured in vitro with cultured cancer cells upon a 72 hour exposure time to the drug. One of ordinary skill in the art can determine the appropriate chemical moiety for $R_1$ and the appropriate position for $R_1$ using only routine experimentation.

For example electron donating groups at the meta position are expected to increase the cytotoxic potency, while substitution at the para position is not expected to increase the potency as compared to the parent taxane. Typically a few representative taxanes with substituents at the different positions (ortho, meta and para) will be initially prepared and evaluated for in vitro cytotoxicity.

The disulfide or thiol-containing substituent can be incorporated into the PEG group that is introduced by reaction at the one of the hydroxyl substituents in the taxane skeleton. The chemistry to protect the various hydroxyl groups, while reacting the desired one, has been described previously (see, for example, the references cited supra). The substituent is introduced by simply converting the free hydroxyl group to a PEG-containing ether, a PEG-containing ester, or a PEG-containing carbamate. This transformation is achieved as follows. The desired hydroxyl group is deprotonated by treatment with the commercially available reagent lithium hexamethyldisilazane (1.2 equivalents) in tetrahydrofuran at −40° C. as described in I. Ojima et al, supra. The resulting alkoxide anion is then reacted with halogenated PEG bearing an appropriately protected thiol substituent, followed by deprotection of the thiol group to provide the desired thiol-containing PEGylated taxane. The thiol group can be converted into a methyl or pyridyl disulfide by reaction with methyl methane thiolsulfonate or dithiodipyridine respectively. This method is described in U.S. Pat. No. 5,416,064.

Figure 4A:
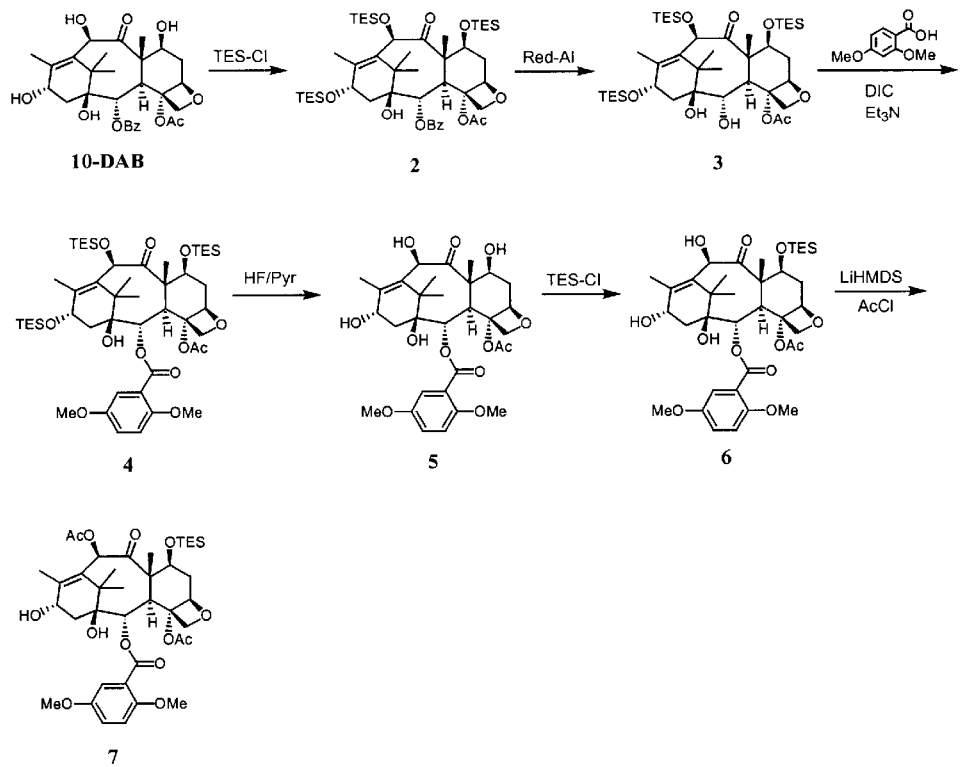
FIGS. 4–8 show the synthetic schemes for the preparation of polyethylene glycol-containing taxanes of the present invention.
Figure 4B:
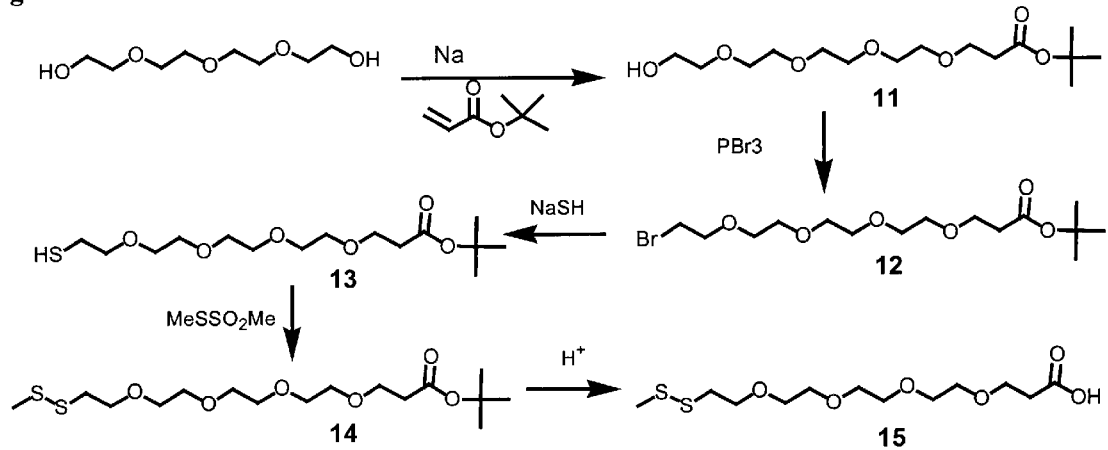
Figure 5:
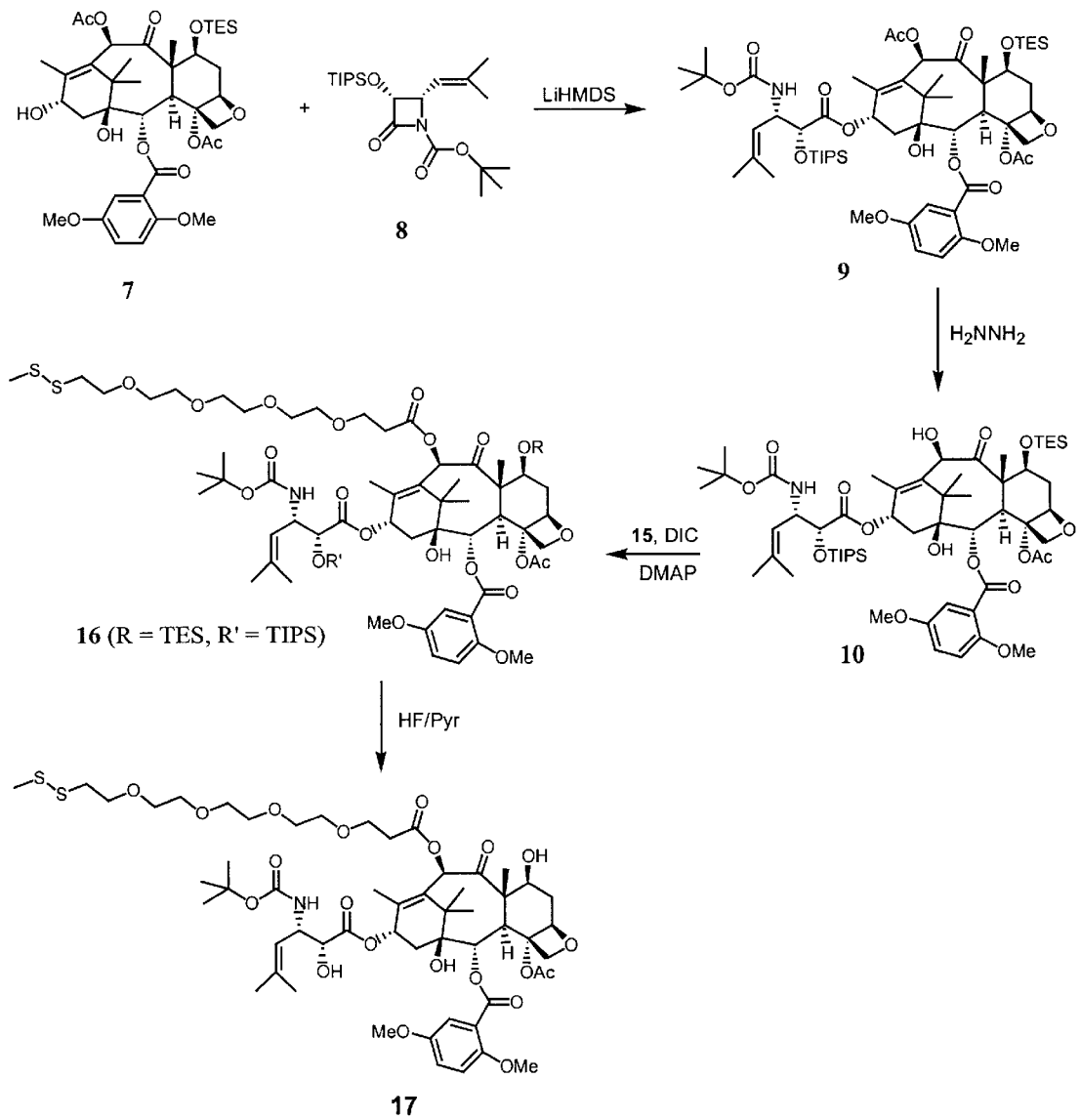
Figure 6:
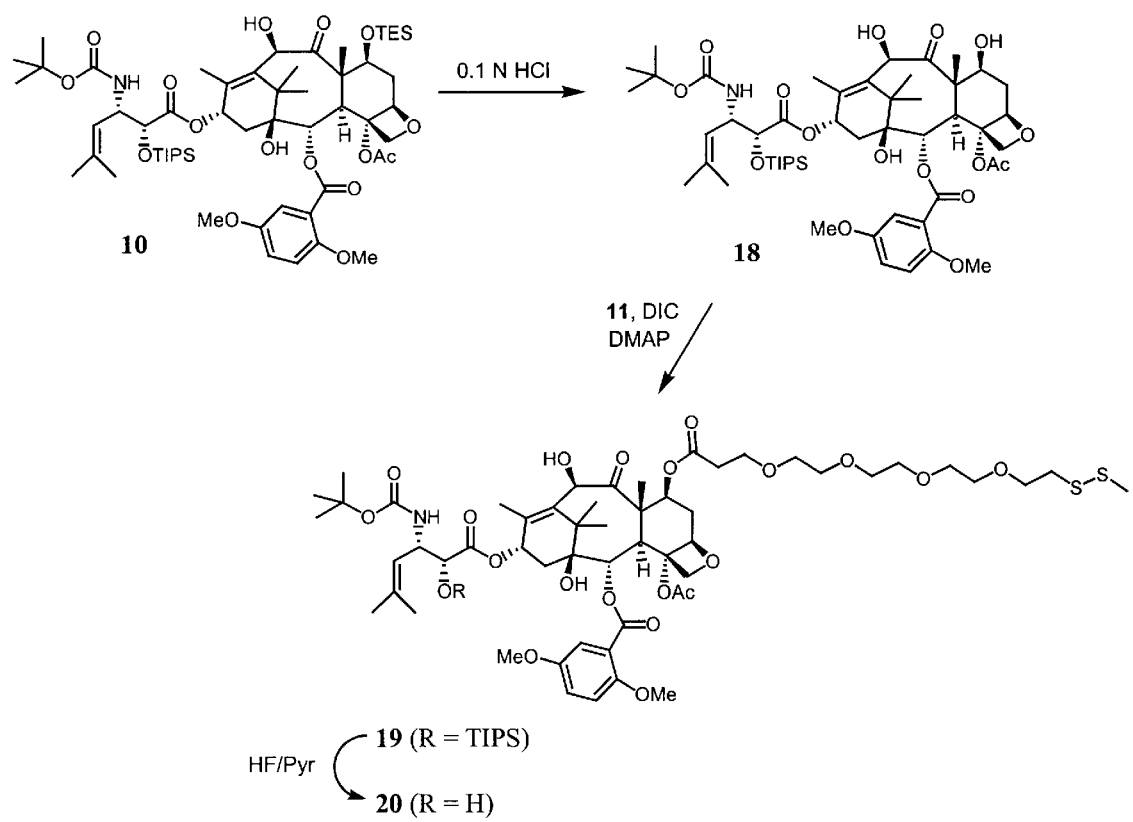
Figure 7:
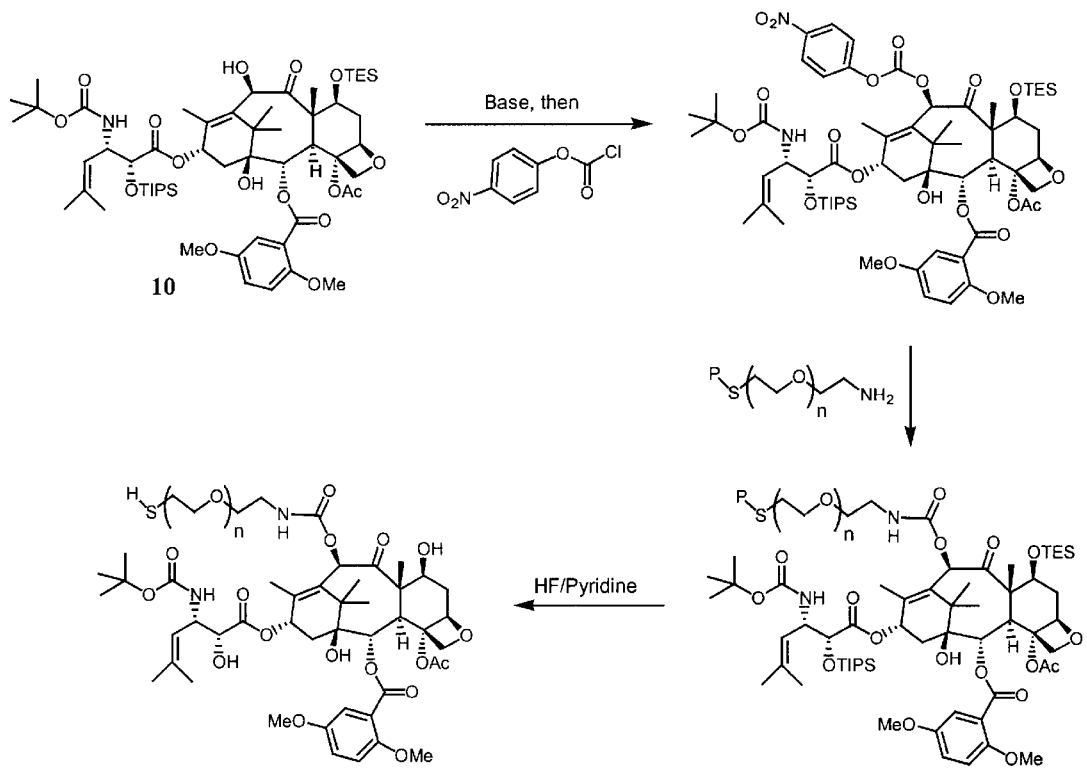
Figure 8:
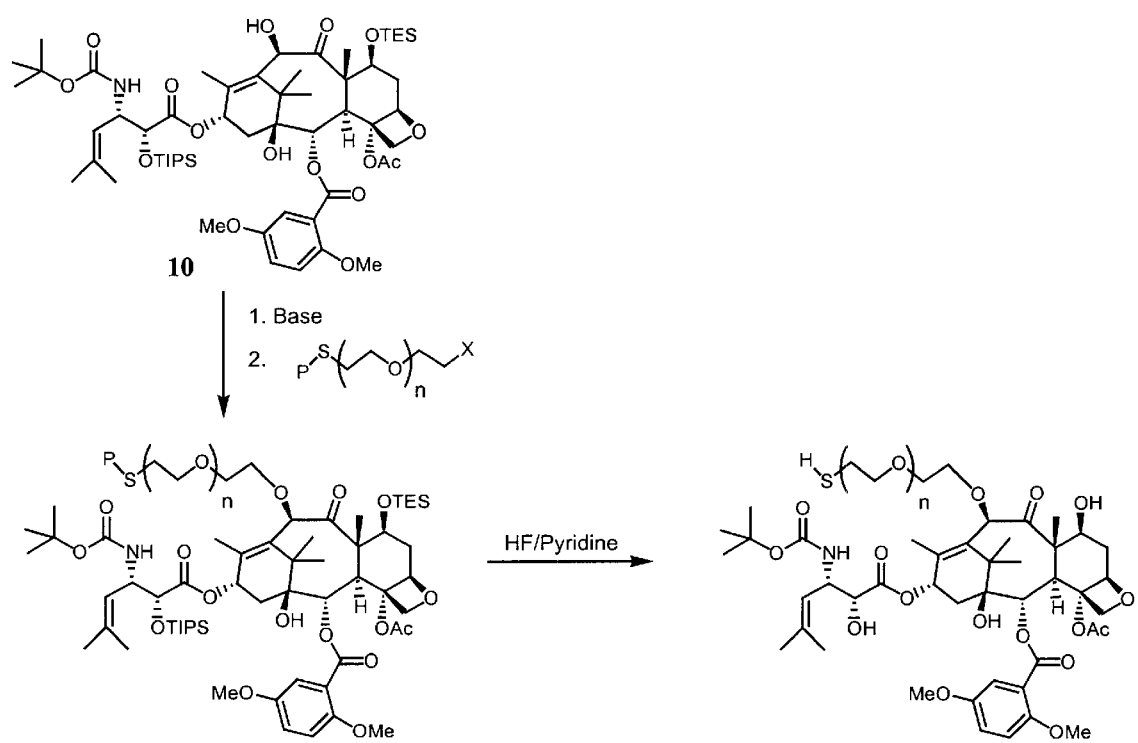

Alternatively, the desired hydroxyl group can be esterified directly by reaction with a carboxy-PEG bearing a disulfide-containing substituent, in the presence of a coupling agent such as di-isopropylcarbodiimide (DIC), to provide a disulfide-containing PEGylated taxane ester. Reduction of the disulfide substituent can then provide the thiol-containing PEGylated taxane ester. In order to prepare disulfide-containing carbamates, the hydroxyl group can be reacted with a commercially available chloroformate, such as para-nitrophenyl chloroformate, followed by reaction with an amino-PEG bearing a disulfide-containing substituent. Representative synthetic schemes are shown in FIGS. 4 to 8 and the methods are described in Example 2.

Disulfide-containing and thiol-containing PEGylated taxane drugs of the invention can be evaluated for their ability to suppress proliferation of various unwanted cell lines in vitro. For example, cell lines such as the human lung carcinoma line A549, the human breast tumor line MCF-7, and the Burkitt's lymphoma line Namalwa can easily be used for the assessment of cytotoxicity of these compounds. Cells to be evaluated can be exposed to the compounds for 72 hours and the surviving fractions of cells measured in direct assays by known methods. $IC_{50}$ values can then be calculated from the results of the assays. Results from the testing of PEGylated taxoids of this invention are shown in FIGS. 9, 10, and 11. PEGylated taxoid 17 is extremely potent with an $IC_{50}$ value of $6.3 \times 10^{-11}$ M towards MCF-7 cells. PEGylated taxoid 17 is shown to have the same high in vitro potency as the corresponding non-PEGylated parent taxoid 1 towards A-431 cells ($IC_{50}$ for both taxoids=$3.3 \times 10^{-10}$ M). Pegylated taxoid 20 is also highly potent, with an $IC_{50}$ value of $3.2 \times 10^{-10}$ M towards MCF-7 cells.

The effectiveness of the compounds of the invention as therapeutic agents depends on the selection of an appropriate cell binding agent. Cell binding agents may be of any kind presently known, or that become known and include peptides and non-peptides. The cell-binding agent may be any compound that can bind a cell, either in a specific or nonspecific manner. Generally, these can be antibodies, or fragments thereof (especially monoclonal antibodies), lymphokines, hormones, growth factors, vitamins, nutrient-transport molecules (such as transferrin), or any other cell binding molecule or substance.

More specific examples of cell binding agents that can be used include:

resurfaced antibodies (U.S. Pat. No. 5,639,641), humanized or fully human antibodies;

single chain antibodies (Oi, V. T. & Morrison, S. 4 *BioTechniques*, 214–221 (1986), Raag, R & Whitlow, M. 9 *FASEB J.* 73–80 (1995), Reiter, Y. et al. 14 *Nature Biotechn.* 1239–12145 (1996));

chimeric antibodies (U.S. Pat. No. 4,816,567):

fragments of antibodies such as sFv, Fab, Fab', and F(ab')$_2$ (Parham, 131 *J. Immunol.* 2895–2902 (1983); Spring et al, 113 *J. Immunol.* 470–478 (1974));

Nisonoff et al, 89 *Arch. Biochem. Biophys.* 230–244 (1960));

interferons (e.g. α, β, γ);

lymphokines such as IL-2, IL-3, IL-4, IL-6;

hormones such as insulin, TRH (thyrotropin releasing hormones), MSH (melanocyte-stimulating hormone), steroid hormnones, such as androgens and estrogens;

vitamins such as folic acid;

growth factors and colony-stimulating factors such as EGF, TGF-α, VEGF, PDGF, FGF, IGF-1, IGF-2, Somatostatin, G-CSF, M-CSF and GM-CSF (Burgess, 5 *Immunology Today* 155–158 (1984)); and transferrin (O'Keefe et al, 260 *J. Biol. Chem.* 932–937 (1985)).

Monoclonal antibody techniques allow for the production of extremely specific cell binding agents in the form of specific monoclonal antibodies or fragments thereof. Particularly well known in the art are techniques for creating monoclonal antibodies, or fragments thereof, by immunizing mice, rats, hamsters, or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies, or fragments thereof, is the use of phage libraries of sFv (single chain variable region), specifically human sFv. (See e.g., Griffiths et al., U.S. Pat. No. 5,885,793; McCafferty et al., WO 92/01047; Liming et al., WO 99/06587).

Selection of the appropriate cell binding agent is a matter of choice that depends upon the particular cell population to be targeted, but in general, monoclonal antibodies are preferred if an appropriate one is available.

For example, the monoclonal antibody MY9 is a murine $IgG_1$ antibody that binds specifically to the CD33 Antigen (J. D. Griffin et al 8 Leukemia Res., 521 (1984)) and can be used if the target cells express CD33 such as in the disease of acute myelogenous leukemia (AML). Similarly, the monoclonal antibody anti-B4 is a murine $IgG_1$, that binds to the CD19 antigen on B cells (Nadler et al, 131 *J. Immunol.* 244–250 (1983)) and can be used if the target cells are B cells or diseased cells that express this antigen, such as in non-Hodgkin's lymphoma or chronic lymphoblastic leukemia. Similarly, the antibody N901 is a murine monoclonal $IgG_1$ antibody that binds to CD56 found on small cell lung carcinoma cells and on cells of other tumors of neuroendocrine origin (Roy et al. *J. Nat. Cancer Inst.* 88:1136–1145 (1996)).

Additionally, GM-CSF, which binds to myeloid cells, can be used as a cell binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma. Folic acid, which targets the folate receptor expressed on ovarian and other cancers, is also a suitable cell binding agent.

Cancers of the breast and testes can be successfully targeted with estrogen (or estrogen analogues) or androgen (or androgen analogues), respectively, as cell binding agents.

Conjugates of the PEGylated taxanes of the invention and a cell binding agent can be formed using any techniques presently known or later developed. Numerous methods of conjugation are taught in U.S. Pat. No. 5,416,064 and U.S. Pat. No. 5,475,092. The PEGylated taxane ester can be modified to yield a free amino group and then linked to an antibody or other cell binding agent via an acid labile linker or a photolabile linker. The PEGylated taxane ester can be condensed with a peptide and subsequently linked to a cell binding agent to produce a peptidase labile linker. The hydroxyl group on the PEGylated taxane ester can be succinylated and linked to a cell binding agent to produce a conjugate that can be cleaved by intracellular esterases to liberate free drug. Most preferably, the PEGylated taxane ethers, esters, or carbamates are treated to create a free or protected thiol group, and then the disulfide- or thiol-containing taxanes are linked to the cell binding agent via disulfide bonds.

Representative conjugates of the invention are antibody-PEGylated-taxane, antibody fragment-PEGylated-taxane, epidermal growth factor (EGF)-PEGylated-taxane, (TGF-α)-PEGylated-taxane, (FGF)-PEGylated-taxane, (PDGF)-PEGylated-taxane, melanocyte stimulating hormone (MSH)-PEGylated-taxane, (IGF-1)-PEGylated-taxane, (IGF-2)-PEGylated-taxane, (Somatostatin)-PEGylated-taxane, thyroid stimulating hormone (TSH)-PEGylated-taxane, estrogen-PEGylated-taxane, estrogen analogue-PEGylated-taxane, androgen-PEGylated-taxane, androgen analogue-PEGylated-taxane, and folate-PEGylated-taxane.

PEGylated-taxane conjugates of antibodies, antibody fragments, protein or peptide hormones, protein or peptide growth factors and other proteins are made in the same way by known methods. For example, peptides and antibodies can be modified with cross linking reagents such as N-succinimidyl 3-(2-pyridyldithio)propionate (SPDP), N-succinimidyl 4-(2-pyridyldithio)pentanoate (SPP), 4-succinimidyl-oxycarbonyl-α-methyl-α-(2-pyridyl dithio)-toluene (SMPT), N-succinimidyl-3-(2-pyridyldithio) butyrate (SDPB), 2-iminothiolane, or S-acetylsuccinic anhydride by known methods. See, Carlsson et al, 173 *Biochem. J.* 723–737 (1978); Blattler et al, 24 *Biochem.* 1517–1524 (1985); Lambert et al, 22 *Biochem.* 3913–3920 (1983); Klotz et al, 96 *Arch. Biochem. Biophys.* 605 (1962); and Liu et al, 18 *Biochem.* 690 (1979), Blakey and Thorpe, 1 *Antibody, Immunoconjugates and Radiopharmaceuticals*, 1–16 (1988), Worrell et al 1 *Anti-Cancer Drug Design* 179–184 (1986). The free or protected thiol-containing cell binding agent thus derived is then reacted with a disulfide- or thiol-containing taxane to produce conjugates. The conjugates can be purified by HPLC or by gel filtration.

Similarly, for example, estrogen and androgen cell binding agents such as estradiol and androstenediol can be esterified at the C-17 hydroxy group with an appropriate disulfide containing carboxylic acid using e.g., dicyclohexylcarbodiimide as a condensing agent. Examples of such carboxylic acids that can be employed are 3-(2-pyridyldithio) propanoic acid, 3-methyldithiopropanoic acid, 4-(2-pyridyldithio) pentanoic acid, and 3-phenyldithiopropanoic acid. Esterification of the C-17 hydroxy group can also be achieved by reaction with an appropriately protected thiol group containing carboxylic acid chloride such as 3-S-acetylpropanoyl chloride. Other methods of esterification can also be employed as described in the literature (Haslam, 36 *Tetrahedron* 2409–2433 (1980)). The protected or free thiol containing androgen or estrogen can then be reacted with a disulfide- or thiol-containing PEGylated taxane to produce conjugates. The conjugates can be purified by column chromatography on silica gel or by HPLC. Folic acid can be condensed with a suitable hydrazide such as 4-(2-pyridyldithio) pentanoic acid hydrazide in the presence of a condensing agent such as dicyclohexyl carbodiimide to give a hydrazone containing an active disulfide. The disulfide-containing folate can then be reacted with a thiol-containing taxane to produce a conjugate that can be purified by column chromatography over silica gel or by HPLC Preferably monoclonal antibody- or cell binding agent-PEGylated-taxane conjugates are those that are joined via a disulfide bond, as discussed above, that are capable of delivering the PEGylated taxane molecules. Such cell binding conjugates are prepared by known methods such as by modifying monoclonal antibodies with succinimidyl pyridyl-dithiopropionate (SPDP) (Carlsson et al, 173 *Biochem. J.* 723–737 (1978)). The resulting thiopyridyl group is then displaced by treatment with thiol-containing PEGylated taxanes to produce disulfide linked conjugates. Alternatively, in the case of the aryldithio-taxanes, the formation of the cell binding conjugate is effected by direct displacement of the aryl-thiol of the PEGylated taxane by sulfhydryl groups previously introduced into antibody molecules. Conjugates containing 1 to 10 taxane drugs linked via a disulfide bridge are readily prepared by either method.

More specifically, a solution of the dithiopyridyl modified antibody at a concentration of 1 mg/ml in 0.1 M potassium phosphate buffer, at pH 6.5 containing 1 mM EDTA is treated with the thiol-containing PEGylated taxane (1.7 molar eq./dithiopyridyl group). The release of thiopyridine from the modified antibody is monitored spectrophotometrically at 343 nm and is complete in about 20 hours. The antibody-taxane conjugate is purified and freed of unreacted drug and other low molecular weight material by gel filtration through a column of Sephadex G-25 or Sephacryl S300. The number of taxane moieties bound per antibody molecule can be determined by measuring the ratio of the absorbance at 230 nm and 275 nm. An average of 1–10 taxane molecules/antibody molecule can be linked via disulfide bonds by this method.

Antibody-PEGylated taxane conjugates with non-cleavable links can also be prepared. The antibody can be modified with crosslinking reagents such as succinimidyl 4-(maleimidomethyl)cyclohexane-1-carboxylate (SMCC), sulfo-SMCC, m-nmaleimnidobenzoyl-N-hydroxysuccinimide ester (MBS), sulfo-MBS or succinimidyl-iodoacetate, as described in the literature, to introduce 1–10 reactive groups. See, Yoshitake et al, 101 *Eur. J. Biochem.* 395–399 (1979); Hashida et al, *J. Applied Biochem.* 56–63 (1984); and Liu et al, 18 *Biochem.* 690–697 (1979). The modified antibody is then reacted with the thiol-containing taxane derivative to produce a conjugate. The conjugate can be purified by dialysis, or by gel filtration through a Sephadex G-25 or Sephacryl S-300 column.

The modified antibodies, or fragments thereof, are treated with the thiol-containing PEGylated taxanes (1.25 molar equivalent/maleimido group). The mixtures are incubated overnight at ambient temperature. The antibody-taxane conjugates are purified by dialysis, or by gel filtration through a Sephadex G-25 or Sephacryl S-300 column. Typically, an average of 1 to 10 taxanes per antibody are linked.

A preferred method is to modify antibodies, or fragments thereof, with succinimidyl-4-(maleimidomethyl)-cyclohexane-1-carboxylate (SMCC) to introduce maleimido groups followed by reaction of the modified antibody or fragment with the thiol-containing PEGylated taxanes to give a thioether linked conjugate. Again, conjugates with 1 to 10 drug molecules per antibody molecule result.

Cytotoxicity of the PEGylated taxanes and their antibody conjugates to non-adherent cell lines such as Namalwa and HL-60 can be measured by back-extrapolation of cell proliferation curves as described in Goldmacher et al, 135 *J. Immunol.* 3648–3651 (1985). Cytotoxicity of these compounds to adherent cell lines such as $SKBR_3$ and A431 can be determined by clonogenic assays as described in Goldmacher et al, 102 *J. Cell Biol.* 1312–1319 (1986).

The present invention also provides a therapeutic composition comprising:

(A) an effective amount of a cytotoxic agent comprising one or more taxanes linked to a cell binding agent through a polyethylene glycol-containing linking group at C-7 or C-10 of at least one of the taxanes; and (B) a pharmaceutically acceptable carrier, diluent, or excipient.

Similarly, the present invention provides a method of killing selected cell populations comprising contacting the target cells or tissue containing target cells with a cytotoxic amount of the above-described cytotoxic agent.

The cytotoxic agent is prepared as described above.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20.

The method for killing selected cell populations can be practiced in vitro, in vivo, or ex vivo.

Examples of in vitro uses include treatments of autologous bone marrow prior to their transplant into the same patient in order to kill diseased or malignant cells; treatments of bone marrow prior to their transplantation in order to kill competent T cells and prevent graft-versus-host-disease (GVHD); treatments of cell cultures in order to kill all cells except for desired variants that do not express the target antigen or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 $\mu$M to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 100 ml of normal saline to which 5 to 10 ml of human serum albumin can be added. Dosages will be 10 $\mu$g to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

EXAMPLES

The invention will now be illustrated by reference to non-limiting examples. Unless otherwise stated, all percents, ratios, parts, etc. are by weight.

Example 1

In Vitro Cytotoxicity Assays

The sulfide, disulfide, and sulfhydryl containing PEGylated taxane drugs of the invention can be evaluated for their ability to suppress proliferation of various human tumor cell lines in vitro. Two adherent cell lines A549(human lung carcinoma) and MCF-7 (human breast tumor) and the non-adherent cell line, Namalwa (Burkitt's lymphoma) are used for the assessment of cytotoxicity of these compounds. Cells are exposed to the compounds for 72 hours and the surviving fractions of cells are measured in direct assays. (A549 and MCF-7 are assayed for plating efficiency (Goldmacher et al, 102 *J. Cell. Biol.* 1312–1319 (1986) and Namalwa are assayed by growth back extrapolation (Goldmacher et al, 135 *J. Immunol.* 3648–3651 (1985)). $IC_{50}$ values are then calculated from this data.

Example 2

Synthesis of Pegylated Taxanes

Materials and Methods

Melting points were measured using an Electrothermal apparatus and are uncorrected. NMR spectra were recorded on a Bruker AVANCE400 (400 MHz) spectrometer. Chemical shifts are reported in ppm relative to TMS as an internal standard. Mass spectra were obtained using a Bruker Esquire 3000 system. Ultraviolet spectra were recorded on a Hitachi U1200 spectrophotometer. HPLC was performed using a Beckman Coulter GOLD 125 system equipped with a Beckman Coulter system GOLD 168 variable wavelength detector and a VYDAC reverse phase C-18 column. Thin layer chromatography was performed on Analtech GF silica gel TLC plates. Silica gel for flash column chromatography was from Baker. Tetrahydrofuran was dried by distillation over sodium metal. Dimethylactamide and dimethylformamide were dried by distillation over calcium hydride under reduced pressure. All other solvents used were reagent grade or HPLC grade.

7,10,13-Tri(triethylsilyl)-10-deacetylbaccatin III (2)—To a solution of 10-DAB (1) (2.64 g, 4.85 mmol) and imidazole (1.65 g, 24.3 mmol) in dry N,N-dimethylformamide (DMF, 8 mL) was added chlorotriethylsilane (4.89 mL, 29.1 mmol) dropwise via syringe at room temperature. The reaction mixture was stirred for 48 h at room temperature and diluted with ethyl acetate (300 mL). The mixture was then washed with ammonium chloride (100 mL×3), water (100 ml), brine (100 mL), dried over anhydrous magnesium sulfate and concentrated in vacuo. The crude product was purified on a silica gel column using 20% ethyl acetate in hexane as the eluant to give 2 as a white solid (4.08 g, 95%): mp 187–189° C.; $^1$H NMR (CDCl$_3$) δ 0.65 (m, 18H), 0.99 (m, 27H), 1.11 (s, 3H), 1.18 (s, 3H), 1.64 s, 3H), 1.87 (m, 1H), 1.97 (s, 3H), 2.08 (dd, J=15.2, 8.8 Hz, 1H), 2.21 (dd, J=15.1, 8.2 Hz, 1H), 2.27 (s, 3H), 2.51 (m, 1H), 3.84 (d, J=7.0 Hz, 1H), 4.13 (d, J=8.3 Hz, 1H), 4.27 (d, J=8.3 Hz, 1H), 4.40 (dd, J=10.5, 6.6 Hz, 1H), 4.92 (m, 2H), 5.18 (s, 1H), 5.61 (d, J=7.1 Hz, 1H), 7.44 (t, J=7.3 Hz, 2H), 7.57 (t, J=7.3 Hz, 1H), 8.07 (d, J=7.4 Hz, 1H); $^{13}$C NMR (CDCl$_3$) δ 4.7, 5.2, 5.9, 6.9, 10.4, 14.8, 20.5, 22.4, 26.3, 37.3, 19.8, 42.4, 46.8, 58.2, 68.3, 72.6, 75.4, 75.7, 76.6, 79.5, 80.7, 83.9, 128.5, 129.6, 130.0, 133.4, 135.7, 139.3, 167.1, 169.7, 205.6. m/z LC/MS for $C_{47}H_{78}O_{10}Si_3Na^+$: calcd: 909.48; found: 909.28.

7,10,13-Tri(triethylsilyl)-2-debenzoyl-10-deacetylbaccatin III (3)—To a solution of 2 (1.43 g, 1.59 mmol) in dry THF (80 mL) at −10° C. was added dropwise a solution of Red-Al in toluene (1.9 mL, 65% wt), and the reaction mixture was stirred for 60 min at −10° C. The reaction was quenched with aqueous saturated ammonium chloride solution (150 mL), and the aqueous layer was extracted with ethyl acetate (75 ml×3). The combined extracts were then dried over anhydrous magnesium sulfate and concentrated in vacuo. The residue was purified on a silica gel column using 25% ethyl acetate in hexane as the eluant to afford 3 as a white solid (1.21 g, 97%.): mp 68–70° C.; $^1$H NMR (CDCl$_3$) δ 0.57 (m, 18H), 0.94 (m, 27H), 1.11 (s, 3H), (s, 3H), 1.87 (m, 1H), 1.88 (s, 3H), 1.94 (m, 1H), 2.00 (m, 1H), 2.12 (s, 3H), 2.47 (m, 1H), 3.42 (d, J=6.6 Hz, 1H), 3.80 (d, J=6.6 Hz, 1H), 4.31 (dd, J=10.4, 6.5 Hz, 1H), 4.50 (d, J=9.0 Hz, 1H), 4.57 (d, J=9.1 Hz, 1H), 4.63 (s, 1H), 4.89 (d, J=8.3 Hz, 1H), 4.91 (m, 1H), 5.08 (s, 1H); $^{13}$C NMR (CDCl$_3$) δ0 4.7, 5.1, 5.8, 6.7, 6.8, 10.5, 14.4, 20.5, 22.3, 37.3, 40.3, 42.5, 58.1, 65.0, 66.3, 72.6, 74.6, 75.7, 77.9, 78.5, 81.9, 83.7, 126.8, 127.4, 128.4, 135.9, 138.9, 169.6, 206.3. m/z LC/MS for $C_{40}H_{74}O_9Si_3Na^+$: calcd: 805.45; found: 805.33.

7,10,13-Tri(triethylsilyl)-2-debenzoyl-2-(2,5-dimethoxybenzoyl)-10-deacetylbaccatin III (4)—A solution of 3 (366 mg, 0.468 mmol), 2,5-Dimethoxy benzoic acid (892 mg, 4.9 mmol), DCC (1.0 g, 4.9 mmol), and 4-pyrrolidinopyridine (10 mg, 0.07 mmol) in toluene (4 mL) was stirred for 24 h at 60 degrees. The reaction was monitored by tlc using 40% ethyl acetate in hexane. After cooling to room temperature, the reaction was diluted with 10 mL of 20% ethyl acetate in hexane and passed through a short pad of silica gel using 200 mL of the same solution to wash the silica, and the resulting filtrate was concentrated. The crude residue obtained was purified on a silica gel column using 40% ethyl acetate in hexane as the eluant to give 4 as a white solid, which contained small amounts of DCC and acid. The product was used without further purification. A small sample was purified the same way to yield a pure analytical sample. $^1$H NMR (CDCl$_3$) 6 $^1$H NMR (CDCl$_3$) δ 0.60 (m, 18H), 0.90 (m, 27H), 1.13 (s, 3H), 1.16 (s, 3H), 1.64 (s, 3H), 1H), 1.94 (s, 3H), 2.13 (s, 3H), 2.22 (m, 2H), 2.35 (s, 3H), 2.43 (m, 2H), 3H), 3.78 (d, J=7.1 Hz, 1H), 3.85 (s, 3H), 4.24 (d, J=2.0 Hz, 1H), 4.27 (m, 2 H 4.35 (dd, J=6.4, 10.4 Hz, 1H), 4.88 (d, J=8.0 Hz, 1H), 4.96 (t, J=8.0 Hz, 1H), 5.15 (s, 1H), 5.60 (d, J=6.4 Hz, 1H), 6.91 (d, J=8.9 Hz, 1H), 7.02 (dd, J=8.9, 3.4 Hz, 1H), 7.38 (d, J=3.4 Hz 1H). m/z LC/MS for $C_{49}H_{82}O_{12}Si_3Na^+$: calcd: 969.50; found: 969.39.

2-Debenzoyl-2-(2,5-dimethoxybenzoyl)-10-deacetylbaccatin III (5)—To the crude solution of 4 (~400 mg) in pyridine-acetonitrile (1/1, 30 mL) was added dropwise HF/pyridine (70:30, 5 mL) at 0° C., and the mixture was stirred for 24 h with warming to room temperature. The reaction was quenched with saturated aqueous sodium bicarbonate. The reaction mixture was then diluted with ethyl acetate (60 mL), washed with saturated aqueous copper sulfate (20 mL×2) and water (20 mL), dried over anhydrous magnesium sulfate and concentrated in vacuo to afford 2-debenzoyl-2-(2,5-Dimethoxybenzoyl)-10-deacetylbaccatin III, 5 as a white solid (198 mg, 62% yield for 2 steps. $^1$H NMR (CDCl$_3$) δ 1.09 (s, 3H), 1.12 (s, 3H), 1.77 (s, 3H), 1.83 (m, 1H), 2.06 (m, 4H), 2.15 (s, 3H), 2.27 (m, 2H), 2.58 (m, 2H), 3.81 (s,3H), 3.89 (s, 3H), 3.93 (d, J=6.8 Hz, 1H), 4.18 (d, J=2.0 Hz, 1H), 4.24 (m, 1H), 4.33 (m, 2H), 4.92 (m, 2H), 5.30 (s, 1H), 5.62 (d, J=6.8 Hz, 1H), 6.93 (d, J=8.9 Hz, 1H), 7.06 (dd, J=8.9, 3.4 Hz, 1H), 7.38 (d, J=3.4 Hz 1H). m/z LC/MS for $C_{31}H_{40}O_{12}Na^+$: calcd: 627.25; found: 627.31.

7-Triethylsilyl-2-debenzoyl-2-(2,5-dimethoxybenzoyl)-10-deacetylbaccatin III (6)—To a solution of 5 thus obtained (86 mg, 0.139 mmol) and imidazole (40 mg, 0.556 mmol) in dry DMF (4 mL) was added chlorotriethylsilane (70 μL, 0.420 mmol) via syringe at 0° C. The ice bath was removed and the reaction mixture was stirred for 3 h at rt and diluted with ethyl acetate (50 mL). The mixture was then washed with aqueous ammonium chloride (25 mL×2), brine (25 mL), dried over anhydrous magnesium sulfate and concentrated in vacuo. The crude product was purified on a silica gel column using 60% ethyl acetate in hexane as the eluant to give 6 as a white solid (87 mg, 88%): $^1$H NMR (CDCl$_3$) δ 0.54 (m, 6H), 0.90 (t, J=8.0 Hz, 9H), 1.02 (s, 3H), 1.08 (s, 3H), 1.72 (s, 3H), 1.86 (m, 1H), 2.10 (m, 4H), 2.13 (s, 3H), 2.22 (m, 2H), 2.43 (m, 1H), 2.58 (s, 1H), 2.72 (m, 1H), 3.78 (s, 3H), 3.86 (d, J=7.1 Hz, 1H), 3.87 (s, 3H), 4.25 (d, J=2.0 Hz, 1H), 4.29 (m, 2H), 4.35 (dd, J=6.4, 10.4 Hz, 1H), 4.84 (br t, 1H), 4.91 (d, J=8.6 Hz, 1H), 5.13 (d, J=2.0 Hz, 1H), 5.56 (d, J=6.8 Hz, 1H), 6.91 (d, J=8.9 Hz, 1H), 7.04 (dd, J=8.9, 3.4 Hz, 1H), 7.37 (d, J=3.4 Hz 1H). m/z LC/MS for $C_{37}H_{54}O_{12}SiNa^+$: calcd: 741.34; found: 741.39.

7-Triethylsilyl-2-debenzoyl-2-(2,5-dimethoxybenzoyl) baccatin III (7)—To a solution of 6 (87 mg, 0.121 mmol) in dry THF (7 mL) was added 1.0 M LiHMDS in THF (170 μL, 0.170 mmol) dropwise via syringe at −40° C. The mixture was stirred at −40° C. for 5 min, and freshly distilled acetyl chloride (12 μL, 0.170 mmol) was added. After 2 hr at −40° C., the reaction was quenched with saturated aqueous ammonium chloride (5 mL), extracted with dichloromethane (10 mL×3). The combined extracts were dried over anhydrous magnesium sulfate and concentrated in vacuo. The crude product was purified on a silica gel column using 60% ethyl acetate in hexane as the eluant to afford 7 as a white solid (70 mg, 77% yield): $^1$H NMR (CDCl$_3$) δ 0.55 (m, 6H), 0.91 (t, J=8.0 Hz, 9H), 1.06 (s, 3H), 1.18 (s, 3H), 1.70 (s, 3H), 1.72 (m, 1H), 1.86 (m, 1H), 2.15 (s, 3H), 2.17 (s, 2.22 (m, 3H), 2.49 (m, 1H), 2.61 (s, 1H), 3.80 (s, 3H), 3.81 (d, J=7.1 Hz, 1H), 3.88 (s, 3H), 4.28 (d, J=8.4 Hz, 1H), 4.31 (d, J=8.4 Hz, 1H), 4.44 (dd, J=6.4 10.4 Hz, 1H), 4.84 (br t, 1H), 4.91 (d, J=8.6 Hz, 1H), 5.61 (d, J=6.4 Hz, 1H), 6.43 (s, 1H), 6.93 (d, J=9.2 Hz, 1H), 7.06 (dd, J=9.2, 3.2 Hz, 1H), 7.37 (d, J=3.2 Hz 1H). m/z LC/MS for C$_{39}$H$_{56}$O$_{13}$SiNa$^+$: calcd: 783.35; found: 783.36.

7-(Triethylsilyl)-2'-(triisopropylsilyloxy)-3'-dephenyl-3'-(isobutenyl)-2-debenzoyl-2-(2,5-dimethoxybenzoyl)-10-acetyl-docetaxel (9)—To a solution of 7 (70 mg, 0.092 mmol) and β-lactam 8 (52 mg, 0.13 mmol) in dry THF (7 mL) was added a solution of 1.0 M LiHMDS in THF (0.13 mL, 0.13 mmol) dropwise at −40° C., and the solution was stirred at −40° C. for 3 hours. The reaction was quenched with saturated aqueous ammonium chloride (10 mL), and the aqueous layer was extracted with ethyl acetate (15 ml×3). The combined extracts were dried over anhydrous magnesium sulfate and concentrated in vacuo. The residue was purified on a silica gel column using 40% ethyl acetate in hexane as the eluant to afford the coupled product 9 as a white solid (62 mg, 61%): $^1$H NMR (CDCl$_3$) δ 0.55 (m, 6H), 0.91 (t, J=8.0 Hz, 9H), 1.11 (m, 27H), 1.20 (s, 3H), 1.23 (s, 3H), 1.37 (m, 10H), 1.6 (s, 3H), 1.72 (m, 6H), 1.89 (m, 1H), 1.98 (s, 3H), 2.15 (s, 3H), 2.17 (s, 3H), 2.17 (s, 3H), 2.34 (m, 1H), 2.49 (m, 2H), 3.74 (d, J=6.8 Hz, 1H), 3.80 (s, 3H), 3.96 (s, 3H), 4.27 (d, J=8.0 Hz, 1H), 4.41 (m, 3H), 4.75 (t, J=8.0 Hz, 1H), 4.88 (m, 2H), 5.34 (d, J=8.4 Hz, 1H), 5.67 (d, J=6.8 Hz, 1H), 6.07 (t, J=9.0 Hz, 1H), 6.45 (s, 1H), 6.93 (d, J=9.2 Hz, 1H), 7.05 (dd, J=9.2, 3.2 Hz, 1H), 7.29 (d, J=2.8 Hz 1H). m/z LC/MS for C$_{60}$H$_{95}$NO$_{17}$Si$_2$Na$^+$: calcd: 1180.61; found: 1180.47.

7-(Triethylsilyl)-2'-(triisopropylsilyloxy)-3'-dephenyl-3'-(isobutenyl)-2-debenzoyl-2-(2,5-dimethoxybenzoyl)-docetaxel (10)—To a solution of 9 (36 mg, 0.031 mmol) in ethanol (1.5 mL) was added hydrazine monohydrate (1 mL) at room temperature. The reaction was stirred at rt and monitored by tlc using 40% ethyl acetate in hexane (developed twice). After 1 hour the reaction was complete by tlc and quenched with saturated aqueous ammonium chloride (10 mL). The aqueous layer was extracted with ethyl acetate (10 ml×3). The combined extracts were dried over anhydrous magnesium sulfate and concentrated in vacuo. The residue was purified on a silica gel column using 35% ethyl acetate in hexane as the eluant to afford the deacetylated product 10 as a white solid (19 mg, 57%): $^1$H NMR (CDCl$_3$) δ 0.56 (m, 6H), 0.92 (t, J=8.0 Hz, 9H), 1.11 (m, 27H), 1.22 (s, 3H), 1.23 (s, 3H), 1.38 (m, 10H), 1.69 (s, 3H), 1.72 (m, 3H), 1.78 (s, 3H), 1.89 (s, 3H), 1.93 (m, 1H), 2.18 (s, 3H), 2.32 (m, 2H), 2.44 (m, 2H), 3.81 (s, 3H), 3.82 (d,J=6.8 Hz, 1H), 3.96 (s, 3H), 4.25 (d, J=2.0 Hz, 1H), 4.29 (d, J=8.0 Hz, 1H), 4.34 (dd, J=6.4, 10.4 Hz, 1H), 4.39 (d, J=2.0 Hz, 1H), 4.42 (d, J=8.0 Hz, 1H), 4.76 (t, J=9.2 Hz, 1H), 4.89 (m, 2H), 5.11 (d, J=2.0 Hz, 1H), 5.34 (d, J=8.8 Hz, 1H), 5.64 (d, J=6.4 Hz, 1H), 6.13 (t, J=9.0 Hz, 1H), 6.94 (d, J=9.2 Hz, 1H), 7.06 (dd, J=9.2, 3.2 Hz, 1H), 7.29 (d, J=2.8 Hz 1H). m/z LC/MS for C$_{58}$H$_{93}$NO$_{16}$Si$_2$Na$^+$: calcd: 1138.60; found: 1138.43.

15-Hydroxy-4,7,10,13-tetraoxapentadecanoic acid tert-butyl ester (11)—To 300 mL of anhydrous THF was added 80 mg (0.0025 mol) of sodium metal and 128 mL of tetraethylene glycol (0.94 mol) with stirring. After the sodium had completely dissolved, tert-butyl acrylate (24 mL, 0.33 mol) was added. The solution was stirred for 20 hrs at room temperature and neutralized with 8 mL of 1.0 M HCl. The solvent was removed in vacuo and the residue was suspended in brine (250 mL) and extracted with ethyl acetate (3×125 mL). The combined organic layers were washed with brine (100 mL) then water (100 mL), dried over sodium sulfate, and the solvent was removed. The resulting colorless oil was dried under vacuum to give 77.13 g (73%) of product. $^1$H NMR: 1.40 (s, 9H), 2.49 (t, 2H, J=6.4 Hz), 3.59–3.73 (m, 18H).
* followed from Seitz and Kunz, *J. Org. Chem.*, 1997, 62, 813–826.

15-Bromo-4,7,10,13-tetraoxapentadecanoic acid tert-butyl ester (12)—To a stirred solution of 11 (1.0 g, 3.11 mmol) in 1 mL of pyridine at 0° was slowly added phosphorus tribromide (0.1 16 mL, 1.22 mmol) via syringe. The solution was allowed to stir overnight, at which time the reaction was complete by tlc. Water (25 mL) was poured into the reaction vessel and the organics were extracted into methylene chloride (3×25 mL). The combined organic layers were washed with sodium bicarbonate (25 mL) then brine (25 mL), dried over magnesium sulfate, and the solvent was removed in vacuo. The residue was purified on silica gel using neat ethyl acetate as the eluant to give 400 mg (35%) of pure product. $^1$H NMR: δ 1.37 (s, 9H), 2.43 (t, 2H, J=6.4 Hz), 3.40 (t, 2H, J=6.4 Hz), 3.53–3:61 (m, 12H), 3.64 (t, 2H, J=6.4 Hz), 3.74 (t, 2H, J=6.4 Hz). $^{13}$C NMR: 27.90, 30.13, 36.06, 66.68, 70.17, 70.31, 70.32, 70.39, 70.46, 70.99, 80.22, 170.65. * modified procedure of Bradshaw et al., *J. Het. Chem.*, 1990, 27, 347–349.

15-Mercapto-4,7,10,13-tetraoxapentadecanoic acid tert-butyl ester (13)- A flask was charged with Amberlite ion exchange resin IRA-400(Cl$^-$ form) (1.3 g, 4.94 mmol of Cl$^-$) and a solution of NaSH H$_2$O (0.218 g, 3.9 mmol) dissolved in 8 mL of MeOH was added with stirring. After allowing to stir for one hour, at which time the reaction became cloudy, a solution of triethylamine hydrochloride (0.180 g, 1.30 mmol) in 1.5 mL of MeOH was added. A solution of 12 (0.500 g, 1.3 mmol) in 2 mL of MeOH was then added dropwise and allowed to stir at room temperature for 16 hrs. The resin was then filtered off and 30 mL of 0.5 M HCl was added. The organic layer was separated, and the aqueous layer was extracted into methylene chloride (2×25 mL). The combined organic layers were dried over anhydrous sodium sulfate, and the solvent removed in vacuo. The residue was purified on silica gel using neat ethyl acetate as the eluant to give 250 mg (60% yield) of the thiol 13. $^1$H NMR: 1.41 (s, 9H), 2.46 (t, 2H, J=6.4 Hz), 2.85 (t, 2H, J=6.4 Hz), 3.55–3.62 (m, 12H), 3.64–3.71 (m, 4H). $^{13}$C NMR: 27.98, 36.14, 38.27, 66.77, 69.51, 70.25, 70.27, 70.39, 70.41, 70.48, 70.52, 80.36, 170.77. MS m/z Calculated: 361.17, Found: 361.94.

15-(Methylditio)-4,7,10,13-tetraoxapentadecanoic acid tert-butyl ester (14)—To a solution of 15-mercapto-4,7,10, 13-tetraoxapentadecanoic acid tert-butyl ester (13, 440 mg, 1.30 mmol) in 8 ml of ethanol and 1 ml of NaH$_2$PO$_4$ (0.5 M, pH 7.0) was added drop wise methylmethanethiosulfonate (368 mg, 2.91 mmol) dissolved in 6 ml of THF. After stirred under Ar over night, the mixture was evaporated to dryness and purified with SiO$_2$ chromatography (2:1 EtOAc/Hexane) to yield 336 mg (67%) of the title compound 14. $^1$H NMR (CDCl$_3$) 3.71 (m, 2H), 3.60 (m, 12H), 2.88 (t, 2H, J=6.7 Hz), 2.48 (t, 2H, J=6.1 Hz), 2.40 (s, 3H), 1.43 (s, 9H), MS 407.1 (M+Na)$^+$.

15-(Methyldito)-4,7,10,13-tetraoxapentadecanoic acid (15)—To a solution of 15-(methyldito)-4,7,10,13-tetraoxapentadecanoic acid tert-butyl ester (14, 335 mg, 0.872 mmol) in 10 ml of dichloromethane was added 1 ml of triethylsilane and 2.0 ml of trifluoroacetic acid. After stirred under Ar over night, the mixture was diluted with 10 ml of toluene and evaporated. The mixture was co-evaporated three times with toluene (3×10 ml) to yield 145 mg (51%) of the title compound 15. $^1$H NMR (CDCl$_3$) 3.72–3.64 (m, 14H), 2.87 (m, 2H), 2.61 (t, 2H, J=6.1 Hz), 2.40 (s, 3H); MS 351.07 (M+Na)$^+$.

7-(Triethylsilyl)-2'-(triisopropylsilyloxy)-3'-dephenyl-3'-(isobutenyl)-2-debenzoyl-2-(2,5-dimethoxybenzoyl)-10-(15-methyldithio-4,7,10,13-tetraoxapentadecanoyl)-docetaxel (16)—To a solution of 10 (9 mg, 0.008 mmol) in methylene chloride (0.5 mL) was added DMAP (1 mg), and acid 15 (10 mg, 0.03 mmol, dissolved in 0.5 mL methylene chloride). To this mixture was then added DIC (0.01 5 mL, 0.08 mmol) and the resulting mixture stirred overnight. Tlc analysis revealed new spot plus a lot of starting material so another 1 mg of DMAP and 0.015 mL of DIC added, and stirred an additional 2 days. Upon completion, the reaction was quenched with saturated aqueous ammonium chloride (10 mL) and extracted into methylene chloride (10 ml×3). The combined extracts were dried over anhydrous magnesium sulfate and concentrated in vacuo. The residue was purified on a silica gel column using 50% ethyl acetate in hexane as the eluant to afford the pegylated product 16 as a white solid (5 mg, 46%): $^1$H NMR (CDCl$_3$) δ 0.56 (m, 6H), 0.91 (m, 12H), 1.11 (m, 21H), 1.20 (s, 3H), 1.22 (s, 3H), 1.27 (m, 3H), 1.38 (s, 9H),15.56 (s, 3H), 1.69 (s, 3H), 1.72 (s, 6H), 1.75 (s, 3H), 1.90 (m, 1H), 1.99 (s, 3H), 2.17 (s, 3H), 2.36 (m, 1H), 2.42 (s, 3H), 2.51 (m, 2H), 2.74 (m, 2H), 2.91 (t, J=6.8 Hz, 2H), 3.21 (br s, 1H), 3.66 (m, 12H), 3.75 (t, J=6.8 Hz, 2H), 3.81 (s, 3H), 3.82 (m, 2H), 3.97 (s, 3H), 4.28 (d, J=8.0 Hz, 1H), 4.42 (m, 3H), 4.76 (t, J=6.4 Hz, 1H), 4.88 (m, 2H), 5.35 (d, J=8.0 Hz, 1H), 5.67 (d, J=6.4 Hz, 1H), 6.07 (t, J=8.8 Hz, 1H), 6.46 (s, 1H), 6.94 (d, J=9.2 Hz, 1H), 7.06 (dd, J=9.2, 3.2 Hz, 1H), 7.30 (d, J=2.8 Hz 1H). m/z LC/MS for C$_{70}$H$_{115}$NO$_{21}$Si$_2$S$_2$Na$^+$: calcd: 1148.72; found: 1148.48.

3'-Dephenyl-3'-(isobutenyl)-2-debenzoyl-2-(2,5-dimethoxybenzoyl)-10-(15-methyldithio-4,7,10,13-tetraoxapentadecanoyl)-docetaxel (17)—To a solution of 16 (5 mg, 0.0035 mmol) in pyridine-acetonitrile (1/1, 1.5 mL) was added HF/pyridine (70:30, 0.1 mL) at 0° C., and the mixture was stirred for 24 h with warming to room temperature. The reaction was quenched with saturated aqueous sodium bicarbonate. The reaction mixture was then diluted with ethyl acetate (5 mL×2), the combined organic layers were washed with water (5 mL), dried over anhydrous sodium sulfate and concentrated in vacuo. The residue was purified on a silica gel column using neat ethyl acetate as the eluant to afford the final product 17 as a white solid (2.7 mg, 68%): $^1$H NMR (CDCl$_3$) δ 1.25 (s, 3H), 1.28 (s, 3H), 1.38 (s, 9H), 1.69 (s, 3H), 1.72 (m, 3H), 1.75 (s, 3H), 1.87 (m, 4H), 2.17 (s, 3H), 2.35 (m, 1H), 2.42 (s, 3H), 2.54 (m, 2H), 2.81 (m, 2H), 2.91 (t, J=6.8 Hz, 2H), 3.08 (br s, 1H), 3.24 (d, J=6.8 Hz, 1H), 3.66 (m, 12H), 3.75 (t, J=6.8 Hz, 2H), 3.81 (s, 3H), 3.82 (m, 2H), 3.95 (s, 3H), 4.16 (d, J=8.8 Hz, 1H), 4.29 (d, J=8.0 Hz, 1H), 4.34 (m, 1H), 4.41 (d, J=8.0 Hz, 1H), 4.72 (m, 2H), 4.93 (d, J=8.0 Hz, 1H), 5.35 (br d, J=6.0 Hz, 1H), 5.66 (d, J=6.8 Hz, 1H), 6.16 (t, J=9.0 Hz, 1H), 6.32 (s, 1H), 6.95 (d, J=9.2 Hz, 1H), 7.06 (dd, J=9.2, 3.2 Hz, 1H), 7.30 (d, J=2.8 Hz 1H). m/z LC/MS for C$_{55}$H$_{81}$NO$_{21}$S$_2$Na$^+$: calcd: 1178.47; found: 1178.39.

2'-(Triisopropylsilyoxy)-3'-dephenyl-3'-(isobutenyl)-2-debenzoyl-2-(2,5-dimethoxybenzoyl)-docetaxel (18)—A solution of 5% hydrochloric acid in ethanol (9.0 mL) was added to 10 (86.4 mg, 0.0774 mmol) at 0° C. The mixture was stirred under N$_2$, with gradual warming to room temperature. After 5 h the reaction was quenched with saturated aqueous sodium bicarbonate and extracted into ethyl acetate (25 mL×2). The combined ethyl acetate layers were then washed with water (25 mL×2), dried over anhydrous magnesium sulfate and concentrated in vacuo. The crude residue was purified on a silica gel column with 50% ethyl acetate in hexanes as the eluant. Product 18 was isolated as a white solid (61.5 mg, 79%): $^1$H NMR (CDCl$_3$) δ 1.08 (s, 27H), 1.23 (s, 3H), 1.36 (s, 9H), 1.58 (m, 1H), 1.67 (s, 3H), 1.70 (s, 3H), 1.76 (s, 3H), 1.82 (m, 2H), 1.88 (s, 3H), 2.16 (s, 3H), 2.31 (m, 1H), 2.50 (m, 2H), 3.17 (br s, 1H), 3.79 (s, 3H), 3.85 (d, J=6.4 Hz, 1H), 3.95 (s, 1H), 4.18 (m, 2H), 4.29 (d, J=8.4 Hz, 1H), 4.37 (d, J=2.0 Hz, 1H), 4.41 (d, J=8.4 Hz, 1H), 4.74 (t, J=9.0 Hz, 1H), 4.90 (m, 2H), 5.17 (d, J=1.6 Hz, 1H), 5.32 (d, J=9.2 Hz, 1H), 5.56 (d, J=6.8 Hz, 1H), 6.10 (t, J=8.8 Hz, 1H), 6.93 (d, J=9.2 Hz, 1H), 7.05 (dd, J=9.2, 3.0 Hz, 1H), 7.28 (d, J=3.0 Hz, 1H). m/z LC/MS for C$_{52}$H$_{79}$NO$_{16}$SiNa$^+$: calcd: 1024.52; found: 1024.31.

2'-(Triisopropylsilyoxy)- 3'-dephenyl-3'-(isobutenyl)-2-debenzoyl-2-(2,5-dimethoxybenzoyl)-7-(15-methyldithio-4, 7,10,13-tetraoxapentadecanoyl)-docetaxel (19)—To a solution of 18 (22.8 mg, 0.0229 mmol), EDC (8.73 mg, 0.0475 mmol) and DMAP (2.79 mg, 0.00229 mmol) in methylene chloride (0.9 mL), a solution of 15 (7.5 mg, 0.0229 mmol) in methylene chloride (0.1 mL) was added. The reaction stirred under N$_2$ at room temperature overnight. The reaction was quenched with saturated aqueous ammonium chloride and extracted into methylene chloride (25 mL×2). The combined organic layers were washed with water (15 mL×1), dried over anhydrous magnesium sulfate and concentrated in vacuo. The residue was purified on a silica gel column with 60% ethyl acetate in hexanes as the eluant yielding product 19 (9.4 mg, 0.007 mmol) and significant starting material 18 (11.3 mg, 0.0113 mmol). The starting material was redissolved in methylene chloride (0.9 mL) with EDC (4.3 mg, 0.0226 mmol) and DMAP (1.4 mg, 0.0113 mmol). A solution of 15 (3.33 mg, 0.01 mmol) in methylene chloride (0.1 mL) was added and the reaction stirred under N$_2$ at room temperature for 72 h. Product 19 was extracted and purified as described above and combined with the first fraction (15.3 mg, 51%): $^1$H NMR (CDCl$_3$) δ 1.10 (s, 27H), 1.23 (m, 6H), 1.37 (s, 9H), 1.68 (s, 3H), 1.71 (s, 3H), 1.87 (s, 3H), 1.92 (s, 3H), 2.16 (s, 3H), 2.33 (m, 2H), 2.41 (s, 3H), 2.51 (m, 4H), 2.89 (t, J=6.8 Hz, 2H), 3.20 (br s, 1H), 3.65 (m, 16H), 3.74 (t, J=6.8 Hz, 2H), 3.80 (s, 3H), 3.95 (m, 4H), 4.31 (d, J=8.0 Hz, 1H), 4.38 (d, J=2.0 Hz, 1H), 4.44 (d, J=8.4 Hz, 1H), 4.76 (t, J=9.4 Hz, 1H), 4.90 (m, 2H), 5.28 (s, 1H), 5.3 (d, J=8.8 Hz, 1H), 5.48 (dd, J=7.2, 10.8 Hz, 1H), 5.65 (d, J=6.8 Hz, 1H), 6.11 (t, J=9.2 Hz, 1H), 6.94 (d, J=9.2 Hz, 1H), 7.07 (dd, J=3.2, 9.2 Hz, 1H), 7.28 (d, J=3.2 Hz, 1H). m/z LC/MS for C$_{64}$H$_{101}$NO$_{21}$S$_2$SiNa$^+$: cacld: 1334.61; found: 1334.59.

3'-Dephenyl-3'-(isobutenyl)-2-debenzoyl-2-(2,5-dimethoxybenzoyl)-7-(15-methyldithio-4,7,10,13-tetraoxapentadecanoyl)-docetaxel (20)—Under N$_2$, 19 (15.3 mg, 0.01166 mmol) was dissolved in pyridine-acetonitrile (1/1, 2.0 mL). HF/pyridine (70:30, 0.16 mL) was added at 0° C. and the reaction stirred for 24 h, warming to room temperature. The reaction was quenched with saturated aqueous sodium bicarbonate and extracted into ethyl acetate (20 mL×2). The combined organic layers were washed with water (15 mL×1), dried over anhydrous sodium sulfate and concentrated in vacuo. The crude residue was purified on a silica gel column with 80% ethyl acetate in hexanes as the eluant, yielding 20 (11.8 mg, 87.5%): $^1$H NMR (CDCl$_3$) δ 1.24 (s, 6H), 1.38 (s, 9H), 1.69 (s, 3H), 1.74 (s, 3H), 1.88 (s, 3H), 1.92 (m, 1H), 1.93 (s, 3H), 2.17 (s, 3H), 2.32 (m, 2H), 2.41 (s, 3H), 2.50 (m, 4H), 2.9 (t, J=6.8 Hz, 2H), 3.10 (br s, 1H), 3.28 (d, J=6.4 Hz, 1H), 3.64 (m, 16H), 3.72 (t, J=6.8 Hz, 2H), 3.80 (s, 3H), 3.92 (m, 4H), 4.03 (br s, 1H), 4.15 (dd, J=2.0, 6.4Hz, 1H), 4.29 (d, J=8.0 Hz, 1H), 4.42 (d, J=8.4 Hz, 1H), 4.75 (m, 2H), 4.90 (d, J=8.0 Hz, 1H), 5.28 (s, 1H), 5.33 (br d, J=8.0 Hz, 1H), 5.46 (dd, J=7.2, 10.8 Hz, 1H), 5.64 (d, J=6.4 Hz, 1H), 6.14 (t, J=8.4 Hz 1H), 6.94 (d, J=8.8 Hz, 1H), 7.06 (dd, J=3.2, 8.8 Hz, 1H), 7.29 (d, J=3.2 Hz, 1H). m/z LC/MS for $C_{55}H_{81}NO_{21}S_2Na^+$: calcd: 1178.47; found 1178.38.

Example 3

Conjugation to Antibodies

Conjugation of Thiol-containing PEGylated Taxane to Antibodies via Disulfide Links—The conjugation of thiol-containing PEGylated taxanes to antibodies, or fragments thereof, via disulfide links is performed in two steps. In the first step dithiopyridyl groups are introduced into antibodies or antibody fragments using succinimidyl pyridyldithiopentanoate (SPP) as described by Carlsson et al. The thiopyridyl groups are then displaced by reaction with the thiol-containing taxane to produce a conjugate.

Preparation of Antibody-SS-PEGylated Taxane Conjugates—Antibodies anti-B4, MY9, anti-EGF receptor and N901, or fragments thereof, are modified with SPDP or SPP as described in the literature. Between 1 to 10 dithiopyridyl groups are introduced on the average per antibody molecule.

A solution of the dithiopyridyl modified antibody at a concentration of 1 mg/ml in 0.1 M potassium phosphate buffer pH 6.5 containing 1 mM EDTA at 25° C. is treated with a thiol-containing PEGylated taxane (1.7 molar equivalent/dithiopyridyl group). The release of thiopyridine from the modified antibody or fragment thereof is monitored spectrophotometrically at 343 nm and is found to be complete in about 20 hours. The antibody-taxane conjugate is purified and freed of unreacted drug and other low molecular weight material by gel filtration through a column of Sephadex G-25. The number of taxane molecules bound per antibody molecule is determined by measuring the ratio between the absorbances at 230 nm and 275 nm. An average of 1–10 taxane molecules per antibody molecule can be linked via disulfide bonds by this method.

Conjugation of Thiol-Containing PRGylated Taxane to Antibodies via a Noncleavable Thioether Link—The conjugation of a thiol-containing PEGylated-taxane is performed in two steps. The antibody, or fragment thereof, is first reacted with succinimidyl maleimidomethylcyclohexane carboxylate (SMCC) to introduce maleimido groups. The modified antibody is then reacted with the thiol-containing PEGylated taxane forming thioether links.

Preparation of Antibody-PEGylated Taxane Conjugates (non-cleavable)—Antibodies, anti-B4, MY9, anti-EGF receptor and N901, or fragments thereof, are modified with SMCC as described in the literature.

The modified antibodies or antibody fragments are treated with thiol-containing taxane (1.25 molar equivalent/maleimido group). The mixtures are incubated overnight at 4° C. The antibody-taxane conjugates are purified as described above. Typically, an average of 1–10 taxane molecules per antibody molecule are linked.

Example 4

Other Methods of Linking Pegyiated Taxanes
Acid Labile Linkers

PEGylated Taxanes can be esterified with N-protected amino acids, such as N-tboc-L-alanine in the presence of dicyclohexyl-carbodiimide and dimethylaminopyridine (DMAP) by standard methods described in the chemical literature. Cleavage of the t-boc protecting group with trifluoroacetic acid will give a taxane ester containing a terminal amino group. This amino group containing taxane can be linked to antibodies, or fragments thereof, and other cell binding agents via an acid labile linker as previously described (Blattler et al, 24 Biochemistry, 1517–1524 (1985), U.S. Pat. Nos. 4,542,225, 4,569,789 and 4,764,368).
Photolabile Linker The amino group-containing PEGylated taxane derivative described above can be linked to cell binding agents via a photolabile linker as previously described. (Senter et al, 42 Photochemistry and Photobiology, 231–237 (1985), U.S. Pat. No. 4,625,014).
Peptidase Labile Linker The amino group-containing PEGylated taxane described above can also be linked to cell binding agents via peptide spacer linkers. It has been previously shown that short peptide spacers between drugs and macromolecular protein carriers are stable in serum but are readily hydrolyzed by intracellular lysosomal peptidases (Trouet et al, 79 Proc. Nat'l. Acad. Sci., 626–629 (1982)). The amino group containing taxane can be condensed with peptides such as Ala-Leu, Leu-Ala-Leu or a dimer of Ala-Leu using condensing agents such as 1-[3-(dimethylamino)propyl]-3-ethyl carbodiimide-HCl to give a peptide derivative of the taxane which can then be linked to cell binding agents.
Esterase Labile Linker PEGylated Taxanes can be esterified by reaction of the hydroxyl group with succinic anhydride and then linked to a cell binding agent to produce a conjugate that can be cleaved by intracellular esterases to liberate free drug. (For examples see: Aboud-Pirak et al, 38 Biochem. Pharmacol., 641–648 (1989), Laguzza et al, 32 J. Med. Chem., 549–555 (1989)).

What is claimed is:

1. A taxane comprising a polyethylene glycol-containing linking group at C-7 or C-10, wherein the polyethylene glycol-containing linking group comprises a thiol or disulfide as a linking moiety.

2. The taxane of claim 1, wherein the polyethylene glycol-containing linking group is carried on a side chain that is a linear or branched, aromatic or heterocyclic group.

3. The taxane of claim 1, wherein the polyethylene glycol-containing linking group is cleavable.

4. The taxane of claim 1, wherein the polyethylene glycol-containing linking group is not cleavable.

5. The taxane of claim 1, wherein the substituent comprising the polyethylene glycol-containing linking group is selected from the group consisting of:

$-(CR_{13}R_{14})_l(CH_2)_m(CR_{13}R_{14})_l(OCH_2CH_2)_nO$
$(CR_{13}R_{14})_l(CH_2)_m(CR_{13}R_{14})_lSZ$, $-CO(CR_{13}R_{14})_l$
$(CH_2)_m(CR_{13}R_{14})_l(OCH_2CH_2)_nO(CR_{13}R_{14})_l(CH_2)_m$
$(CR_{13}R_{14})_lSZ$, $-CONR_{12}(CR_{13}R_{14})_l(CH_2)_m$
$(CR_{13}R_{14})_l(OCH_2CH_2)_nO(CR_{13}R_4)_l(CH_2)_m(CR_{13}R_{14})_l$
$SZ$, $-(CR_{13}R_{14})_l(CH_2)_m(CR_{13}R_{14})_l(OCH_2CH_2)_n$
$OCO(CR_3R_{14})_l(CH_2)_m(CR_{13}R_{14})_lSZ$, $-(CR_{13}R_{14})_l$
$(CH_2)_m(CR_{13}R_{14})_l(OCH_2CH_2)_nNR_{12}CO(CR_{13}R_{14})_l$
$(CH_2)_m(CR_{13}R_{14})_lSZ$, $-(CR_{13}R_{14})_l(CH_2)_m(CR_{13}R_{14})_l$
$(OCH_2CH_2)_nOCONR_{12}(CR_{13}R_{14})_l(CH_2)_m(CR_{13}R_{14})_l$

SZ, —CO(CR$_{13}$R$_{14}$)$_l$(CH$_2$)$_m$(CR$_{13}$R$_{14}$)$_l$(OCH$_2$CH$_2$)$_n$ OCO(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$NR$_{12}$CO(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$OCONR$_{12}$(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$OCO(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$NR$_{12}$CO(CR$_{13}$r$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$OCONR$_{12}$(CR$_{13}$R$_{14}$)$_l$(CH$_2$)$_m$(CR$_{13}$R$_{14}$)$_l$SZ, —CO-morpholino-X(OCH$_2$CH$_2$)$_n$SZ, —CO-piperazino-X(OCH$_2$CH$_2$)$_n$SZ, —CO-piperidino-X(OCH$_2$CH$_2$)$_n$SZ, and —CO-N-methylpiperazino-X(OCH$_2$CH$_2$)$_n$SZ, wherein Z is H or SR, X is a linear alkyl or branched alkyl having 1–10 carbon atoms, R and R$_{12}$ are the same or different and represent linear alkyl, branched alkyl or cyclic alkyl having 1 to 10 carbon atoms, or simple or substituted aryl having 1 to 10 carbon atoms or heterocyclic, and R$_{12}$ can in addition be H, R$_{13}$ and R$_{14}$ are same or different and represent H or linear alkyl, branched alkyl or cyclic alkyl having 1 to 10 carbon atoms, or aryl, 1 is 0 or an integer from 1 to 10, m is an integer of 1 to 10, and n is 2 to 1000.

6. A compound of formula (I):

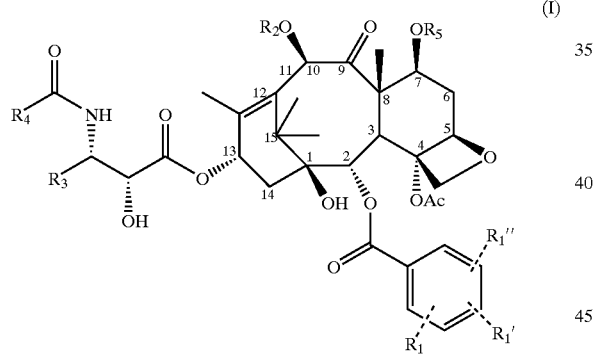

(I)

wherein:

R$_1$ is H, an electron withdrawing group, or an electron donating group;

R$_1$' and R$_1$" are the same or different and are H, an electron withdrawing group, or an electron donating group;

R$_2$ is —(CR$_{13}$R$_{14}$)$_l$(CH$_2$)$_m$(CR$_{13}$R$_{14}$)$_l$(OCH$_2$CH$_2$)$_n$O(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$O(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$O(CR$_{13}$R$_{14}$)$_l$(CH$_2$)$_m$(CR$_{13}$R$_{14}$)$_l$SZ, —(CR$_{13}$R$_{14}$)$_l$(CH$_2$)$_m$(CR$_{13}$R$_{14}$)$_l$(OCH$_2$CH$_2$)$_n$OCO(CR$_{13}$R$_{14}$)$_l$(CH$_2$)$_m$(CR$_{13}$R$_{14}$)$_l$SZ, —(CR$_{13}$R$_{14}$)$_l$(CH$_2$)$_m$(CR$_{13}$R$_{14}$)$_l$(OCH$_2$CH$_2$)$_n$NR$_{12}$CO(CR$_{13}$R$_{14}$)$_l$(CH$_2$)$_m$(CR$_{13}$R$_{14}$)$_l$SZ, —(CR$_{13}$R$_{14}$)$_l$(CH$_2$)$_m$(CR$_{13}$R$_{14}$)$_l$(OCH$_2$CH$_2$)$_n$OCONR$_{12}$(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$OCO(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$NR$_{12}$CO(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$OCONR$_{12}$(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$OCO(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$NR$_{12}$CO(CR$_{13}$R$_{14}$)$_l$)CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$OCONR$_{12}$(CR$_{13}$R$_{14}$)$_l$(CH$_2$)$_m$(CR$_{13}$R$_{14}$)$_l$SZ, —CO-morpholino-X(OCH$_2$CH$_2$)$_n$SZ, —CO-piperazino-X(OCH$_2$CH$_2$)$_n$SZ, —CO-piperidino-X(OCH$_2$CH$_2$)$_n$SZ, and —CO-N-methylpiperazino-X(OCH$_2$CH$_2$)$_n$SZ, wherein Z is H or SR, X is a linear alkyl or branched alkyl having 1–10 carbon atoms, R and R$_{12}$ are the same or different and represent linear alkyl, branched alkyl or cyclic alkyl having 1 to 10 carbon atoms, or simple or substituted aryl having 1 to 10 carbon atoms or heterocyclic, and R$_{12}$ can in addition be H, R$_{13}$ and R$_{14}$ are same or different and represent H or linear alkyl, branched alkyl or cyclic alkyl having 1 to 10 carbon atoms, or aryl, 1 is 0 or an integer from 1 to 10, m is an integer of 1 to 10, and n is 2 to 1000;

R$_3$ is aryl, or is linear, branched or cyclic alkyl having 1 to 10 carbon atoms;

R$_4$ is —OC(CH$_3$)$_3$ or —C$_6$H$_5$; and

R$_5$ is H, a heterocyclic, a linear, branched, or cyclic ester or ether having from 1 to 10 carbon atoms or a carbamate of formula —CNR$_{10}$R$_{11}$, wherein R$_{10}$ and R$_{11}$ are the same or different and are H, linear, branched, or cyclic alkyl having 1 to 10 atoms or simple or substituted aryl having 1 to 10 carbon atoms.

7. A compound of formula (I):

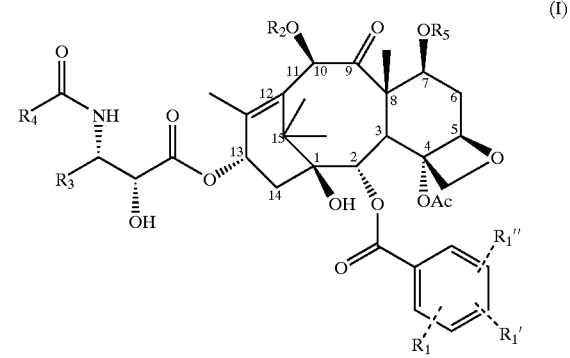

(I)

wherein:

R$_1$ is H, an electron withdrawing group, or an electron donating group;

R$_1$' and R$_1$" are the same or different and are H, an electron withdrawing group, or an electron donating group;

R$_2$ is H, a heterocyclic, a linear, branched, or cyclic ester or ether having from 1 to 10 carbon atoms or a carbamate of the formula —CNR$_{10}$R$_{11}$, wherein R$_{10}$ and R$_{11}$ are the same or different and are H, linear, branched, or cyclic alkyl having 1 to 10 atoms or simple or substituted aryl having 1 to 10 carbon atoms;

R$_3$ is aryl, or is linear, branched or cyclic alkyl having 1 to 10 carbon atoms;

$R_4$ is —OC(CH$_3$)$_3$ or —C$_6$H$_5$; and $R_5$ is —(CR$_{13}$R$_{14}$)$_l$(CH$_2$)$_m$(CR$_{13}$R$_{14}$)$_l$(OCH$_2$CH$_2$)$_n$O(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$O(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$O(CR$_{13}$R$_{14}$)$_l$(CH$_2$)$_m$(CR$_{13}$R$_{14}$)$_l$SZ, —(CR$_{13}$R$_{14}$)$_l$(CH$_2$)$_m$(CR$_{13}$R$_{14}$)$_l$(OCH$_2$CH$_2$)$_n$OCO(CR$_{13}$R$_{14}$)$_l$(CH$_2$)$_m$(CR$_{13}$R$_{14}$)$_l$SZ, —(CR$_{13}$R$_{14}$)$_l$(CH$_2$)$_m$(CR$_{13}$R$_{14}$)$_l$(OCH$_2$CH$_2$)$_n$NR$_{12}$CO(CR$_{13}$R$_{14}$)$_l$(CH$_2$)$_m$(CR$_{13}$R$_{14}$)$_l$SZ, —(CR$_{13}$R$_{14}$)$_l$(CH$_2$)$_m$(CR$_{13}$R$_{14}$)$_l$(OCH$_2$CH$_2$)$_n$OCONR$_{12}$(CR$_{13}$R$_{14}$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$OCO(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$NR$_{12}$CO(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$OCONR$_{12}$(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$OCO(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$NR$_{12}$CO(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$OCONR$_{12}$(CR$_{13}$R$_{14}$)$_l$(CH$_2$)$_m$(CR$_{13}$R$_{14}$)$_l$SZ, —CO-morpholino-X(OCH$_2$CH$_2$)$_n$SZ, —CO-piperazino-X(OCH$_2$CH$_2$)$_n$SZ, —CO-piperidino-X(OCH$_2$CH$_2$)$_n$SZ, and —CO-N-methylpiperazino-X(OCH$_2$CH$_2$)$_n$SZ, wherein Z is H or SR, X is a linear alkyl or branched alkyl having 1–10 carbon atoms, R and R$_{12}$ are the same or different and represent linear alkyl, branched alkyl or cyclic alkyl having 1 to 10 carbon atoms, or simple or substituted aryl having 1 to 10 carbon atoms or heterocyclic, and R$_{12}$ can in addition be H, R$_{13}$ and R$_{14}$ are same or different and represent H or linear alkyl, branched alkyl or cyclic alkyl having 1 to 10 carbon atoms, or aryl, 1 is 0 or an integer from 1 to 10, m is an integer of 1 to 10, and n is 2 to 1000.

8. The compound of claim 6 or 7, wherein R$_1$ is H, F, NO$_2$, CN, Cl, CHF$_2$, CF$_3$, —OCH$_3$, —OCH$_2$CH$_3$, —NR$_7$, or —OR$_8$.

9. The compound of claim 6 or 7, wherein R$_1$ is OMe, OEt, Cl, F, NO$_2$, or CF$_3$.

10. The compound of claim 6 or 7, wherein R$_1$ is in the meta position, R$_1$' is OMe, and R$_1$" is H.

11. The compound of claim 6 or 7, wherein R$_1$' and R$_1$" are the same or different and are H, F, NO$_2$, CN, Cl, CHF$_2$, CF$_3$, —OCH$_3$, OCH$_2$CH$_3$, —NR$_6$R$_7$, or —O$_8$, wherein:

R$_6$ and R$_7$ are the same or different and are each H, linear, branched, or cyclic alkyl groups having 1 to 10 carbon atoms, or simple or substituted aryl having 1 to 10 carbon atoms, and R$_8$ is linear, branched or cyclic alkyl having 1 to 10 carbon atoms.

12. The compound of claim 11, wherein R$_6$ and R$_7$ are same or different and are each H, or are alkyl or aryl having 1 to 4 carbon atoms.

13. The compound of claim 11, wherein —NR$_6$R$_7$ is dimethyl amino, diethyl amino, dipropyl amino, or dibutyl amino, where the butyl moiety is any of primary, secondary, tertiary or isobutyl.

14. The compound of claim 6 or 7, wherein R$_3$ is —CH$_2$CH(CH$_3$)$_2$ or —CH=C(CH$_3$)$_2$.

15. The compound of claim 6 or 7, wherein R$_4$ is —OC(CH$_3$)$_3$ or —C$_6$H$_5$.

16. The compound of claim 6, wherein R$_5$ is H, —COCH$_3$, —COCH$_2$CH$_3$ and —COCH$_2$CH$_2$CH$_3$.

17. The compound of claim 7, wherein R$_2$ is H, —COCH$_3$, —COCH$_2$CH$_3$ and —COCH$_2$CH$_2$CH$_3$.

18. The compound of claim 6, wherein R$_5$ is H, or —CONHCH$_2$CH$_3$, —CONHCH$_2$CH$_2$CH$_3$, —CO-morpholino, —CO-piperazino, —CO-piperidino, or —CO-N-methylpiperazino.

19. The compound of claim 7, wherein R$_2$ is H, or —CONHCH$_2$CH$_3$, —CONHCH$_2$CH$_2$CH$_3$, —CO-morpholino, —CO-piperazino, —CO-piperidino, or —CO-N-methylpiperazino.

20. A cytotoxic agent comprising one or more taxanes linked to a cell binding agent through a polyethylene glycol-containing linking group at C-7 or C-10 of at least one of the taxanes.

21. The cytotoxic agent of claim 20, wherein the polyethylene glycol-containing linking group comprises a thiol or disulfide as the linking moiety.

22. The cytotoxic agent of claim 21, wherein the polyethylene glycol-containing linking group is carried on a side chain that is a linear or branched, aromatic or heterocyclic group.

23. The cytotoxic agent of claim 20, wherein at least one of the taxanes is linked to the cell binding agent through a cleavable linking group.

24. The cytotoxic agent of claim 23, wherein the cleavable linking group is acid labile, photolabile, peptidase labile or esterase labile.

25. The cytotoxic agent of claim 20, wherein at least one of the taxanes is linked to the cell binding agent through a non-cleavable linking group.

26. The cytotoxic agent of claim 20, wherein the substituent comprising the polyethylene glycol-containing linking group is selected from the group consisting of:

—(CR$_{13}$R$_{14}$)$_l$(CH$_2$)$_m$(CR$_{13}$R$_{14}$)$_l$(OCH$_2$CH$_2$)$_n$O(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$O(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$O(CR$_{13}$R$_{14}$)$_l$(CH$_2$)$_m$(CR$_{13}$R$_{14}$)$_l$SZ, —(CR$_{13}$R$_{14}$)$_l$(CH$_2$)$_m$(CR$_{13}$R$_{14}$)$_l$(OCH$_2$CH$_2$)$_n$OCO(CR$_{13}$R$_{14}$)$_l$(CH$_2$)$_m$(CR$_{13}$R$_{14}$)$_l$SZ, —(CR$_{13}$R$_{14}$)$_l$(CH$_2$)$_m$(CR$_{13}$R$_{14}$)$_l$(OCH$_2$CH$_2$)$_n$NR$_{12}$CO(CR$_{13}$R$_{14}$)$_l$(CH$_2$)$_m$(CR$_{13}$R$_{14}$)$_l$SZ, —(CR$_{13}$R$_{14}$)$_l$(CH$_2$)$_m$(CR$_{13}$R$_{14}$)$_l$(OCH$_2$CH$_2$)$_n$OCONR$_{12}$(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$OCO(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$NR$_{12}$CO(CR$_{13}$R$_{14}$)$_l$(CH$_2$)$_m$(CR$_{13}$R$_{14}$)$_l$SZ, —CO(CR$_{13}$R$_{14}$)$_l$(CH$_2$)$_m$(CR$_{13}$R$_{14}$)$_l$(OCH$_2$CH$_2$)$_n$OCONR$_{12}$(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$OCO(CR$_{13}$R$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$NR$_{12}$CO(CR$_{13}$r$_{14}$)$_l$(CH$_2$)$_m$(CR$_{13}$R$_{14}$)$_l$SZ, —CONR$_{12}$(CR$_{13}$R$_{14}$)$_l$(CH$_2$)$_m$(CR$_{13}$R$_{14}$)$_l$(OCH$_2$CH$_2$)$_n$OCONR$_{12}$(CR$_{13}$R$_{14}$)$_l$(CH$_2$)$_m$(CR$_{13}$R$_{14}$)$_l$SZ, —CO-morpholino-X(OCH$_2$CH$_2$)$_n$SZ, —CO-piperazino-X(OCH$_2$CH$_2$)$_n$SZ, —CO-piperidino-X(OCH$_2$CH$_2$)$_n$SZ, and —CO-N-methylpiperazino-X(OCH$_2$CH$_2$)$_n$SZ, wherein Z is H or SR, X is a linear alkyl or branched alkyl having 1–10 carbon atoms, R and R$_{12}$ are the same or different and represent linear alkyl, branched alkyl or cyclic alkyl having 1 to 10 carbon atoms, or simple or substituted aryl having 1 to 10 carbon atoms or heterocyclic, and R$_{12}$ can in addition be H, $R_{13}$ and $R_{14}$ are same or different and represent H or linear alkyl, branched alkyl or cyclic alkyl having 1 to 10 carbon atoms, or aryl, l is 0 or an integer from 1 to 10, m is an integer of 1 to 10, and n is 2 to 1000.

27. The cytotoxic agent of claim 20, wherein the cell binding agent is an antibody or an antibody fragment.

28. The cytotoxic agent of claim 20, wherein the cell binding agent is an antibody, a single chain antibody or a binding fragment of an antibody or single chain antibody.

29. The cytotoxic agent of claim 20, wherein the cell binding agent is a monoclonal antibody, a single chain monoclonal antibody or a binding fragment of a single chain monoclonal antibody a monoclonal antibody which is or is not humanized or resurfaced or chimeric.

30. The cytotoxic agent of claim 29, wherein the cell binding agent binds specifically to the CD33 antigen.

31. The cytotoxic agent of claim 29, wherein the cell binding agent binds specially to the CD56 antigen.

32. The cytotoxic agent of claim 20, wherein the cell binding agent is an interferon, a lymphokines, a hormone, a vitamin, a growth factor, a colony-stimulating factor, or transferrin.

33. The cytotoxic agent of claim 20, wherein the cell binding agent is epidermal growth factor, transforming growth factor, vascular endothelial growth factor, fibroblast growth factor, insulin like growth factor 1 and 2, platelet derived growth factor, melanocyte stimulating hormone, thyroid stimulating hormone, somatostatin, estrogen, estrogen analogue, androgen, androgen analogue, or folate.

34. A therapeutic composition comprising:
(A) An effective amount of a cytotoxic agent comprising one or more taxanes linked to a cell binding agent through a polyethylene glycol-containing linking group at C-7 or C-10 of at least one of the taxanes; and
(B) A pharmaceutically acceptable carrier, diluent, or excipient.

35. The therapeutic composition of claim 34, wherein the polyethylene glycol-containing linking group comprises a thiol or disulfide as the linking moiety.

36. The therapeutic composition of claim 35, wherein the polyethylene glycol-containing linking group is carried on a side chain that is a linear or branched, aromatic or heterocyclic group.

37. The therapeutic composition of claim 34, wherein at least one of the taxanes is linked to the cell binding agent through a cleavable linking group.

38. The therapeutic composition of claim 37, wherein the cleavable linking group is acid labile, photolabile, peptidase labile or esterase labile.

39. The therapeutic composition of claim 34, wherein at least one of the taxanes is linked to the cell binding agent through a non-cleavable linking group.

40. The therapeutic composition of claim 34, wherein the substituent comprising the polyethylene glycol-containing linking group is selected from the group consisting of:

$-(CR_{13}R_{14})_l(CH_2)_m(CR_{13}R_{14})_l(OCH_2CH_2)_nO$
$(CR_{13}R_{14})_l(CH_2)_m(CR_{13}R_{14})_lSZ, -CO(CR_{13}R_{14})_l$
$(CH_2)_m(CR_{13}R_{14})_l(OCH_2CH_2)_nO(CR_{13}R_{14})_l(CH_2)_m$
$(CR_{13}R_{14})_lSZ, -CONR_{12}(CR_{13}R_{14})_l(CH_2)_m$
$(CR_{13}R_{14})_l(OCH_2CH_2)_nO(CR_{13}R_{14})_l(CH_2)_m$
$(CR_{13}R_{14})_lSZ, -(CR_{13}R_{14})_l(CH_2)_m(CR_{13}R_{14})_l$
$(OCH_2CH_2)_nOCO(CR_{13}R_{14})_l(CH_2)_m(CR_{13}R_{14})_lSZ,$
$-(CR_{13}R_{14})_l(CH_2)_m(CR_{13}R_{14})_l(OCH_2CH_2)_nNR_{12}CO$
$(CR_{13}R_{14})_l(CH_2)_m(CR_{13}R_{14})_lSZ, -(CR_{13}R_{14})_l(CH_2)_m$
$(CR_{13}R_{14})_l(OCH_2CH_2)_nOCONR_{12}(CR_{13}R_{14})_l(CH_2)_m$
$(CR_{13}R_{14})_lSZ, -CO(CR_{13}R_{14})_l(CH_2)_m(CR_{13}R_{14})_l$
$(OCH_2CH_2)_nOCO(CR_{13}R_{14})_l(CH_2)_m(CR_{13}R_{14})_lSZ,$
$-CO(CR_{13}R_{14})_l(CH_2)_m(CR_{13}R_{14})_l(OCH_2CH_2)_n$
$NR_{12}CO(CR_{13}R_4)_l(CH_2)_m(CR_{13}R_{14})_lSZ, -CO$
$(CR_{13}R_{14})_l(CH_2)_m(CR_{13}R_{14})_l(OCH_2CH_2)_nOCONR_{12}$
$(CR_{13}R_{14})_l(CH_2)_m(CR_{13}R_{14})_lSZ, -CONR_{12}$
$(CR_{13}R_{14})_l(CH_2)_m(CR_{13}R_{14})_l(OCH_2CH_2)_nOCO$
$(CR_{13}R_{14})_l(CH_2)_m(CR_{13}R_{14})_lSZ, -CONR_{12}$
$(CR_{13}R_{14})_l(CH_2)_m(CR_{13}R_{14})_l(OCH_2CH_2)_nNR_{12}CO$
$(CR_{13}R_{14})_l(CH_2)_m(CR_{13}R_{14})_lSZ, -CONR_{12}$
$(CR_{13}R_{14})_l(CH_2)_m(CR_{13}R_{14}))_l(OCH_2H_2)_nOCONR_{12}$
$(CR_{13}R_{14})_l(CH_2)_m(CR_{13}R_{14})_lSZ, -CO\text{-morpholino-}X$
$(OCH_2CH_2)_nSZ, -CO\text{-piperazino-}X(OCH_2CH_2)_nSZ,$
$-CO\text{-piperidino-}X(OCH_2CH_2)_nSZ,$ and $-CO\text{-N-methylpiperazino-}X(OCH_2CH_2)_nSZ,$ wherein Z is H or SR, X is a linear alkyl or branched alkyl having 1–10 carbon atoms, R and $R_{12}$ are the same or different and represent linear alkyl, branched alkyl or cyclic alkyl having 1 to 10 carbon atoms, or simple or substituted aryl having 1 to 10 carbon atoms or heterocyclic, and $R_{12}$ can in addition be H, $R_{13}$ and $R_{14}$ are same or different and represent H or linear alkyl, branched alkyl or cyclic alkyl having 1 to 10 carbon atoms, or aryl, l is 0 or an integer from 1 to 10, m is an integer of 1 to 10, and n is 2 to 1000.

41. The therapeutic composition of claim 34 or 35, wherein the cell binding agent is an antibody or an antibody fragment.

42. The therapeutic composition of any one of claims 34, 35, 36 or 40, wherein the cell binding agent is an antibody, a single chain antibody or a binding fragment of an antibody or single chain antibody.

43. The therapeutic composition of any one of claims 34, 35, 36 or 40, wherein the cell binding agent is a monoclonal antibody, a single chain monoclonal antibody or a binding fragment of a single chain monoclonal antibody a monoclonal antibody which is or is not humanized or resurfaced or chimeric?.

44. The therapeutic composition of claim 43, wherein the cell binding agent binds specifically to the CD33 antigen.

45. The therapeutic composition of claim 43, wherein the cell binding agent binds specially to the CD19 antigen.

46. The therapeutic composition of any one of claims 34, 35, 36 or 40, wherein the cell binding agent is an interferon, a lymphokine, a hormone, a vitamin, a growth factor, a colony-stimulating factor, or transferrin.

47. The therapeutic composition of any one of claims 34, 35, 36 or 40, wherein the cell binding agent is epidermal growth factor, transforming growth factor, vascular endothelial growth factor, fibroblast growth factor, insulin like growth factor 1 and 2, platelet derived growth factor, somatostatin, melanocyte stimulating hormone, thyroid stimulating hormone, estrogen, estrogen analogue, androgen, androgen analogue, or folate.

48. A method of killing selected cell populations comprising contacting target cells or tissue containing target cells with a cytotoxic amount of the cytotoxic agent of any one of claims 20 to 33.

* * * * *

UNITED STATES PATENT AND TRADEMARK OFFICE
CERTIFICATE OF CORRECTION

| | |
|---|---|
| PATENT NO. | : 6,596,757 B1 |
| APPLICATION NO. | : 10/144042 |
| DATED | : July 22, 2003 |
| INVENTOR(S) | : Ravi V.J. Chari and Michael Louis Miller |

Page 1 of 1

It is certified that error appears in the above-identified patent and that said Letters Patent is hereby corrected as shown below:

Claim 6 (Column 22, lines 27-28): Please delete, and replace with --$R_3$ is aryl, linear, branched or cyclic alkyl having 1 to 10 carbon atoms, or —$CH=C(CH_3)_2$;--

Claim 7 (Column 22, lines 66-67): Please delete, and replace with --$R_3$ is aryl, linear, branched or cyclic alkyl having 1 to 10 carbon atoms, or —$CH=C(CH_3)_2$;--

Claim 15 (Column 23, lines 66-67): Please delete "or —$C_6H_5$"

Signed and Sealed this

Eleventh Day of March, 2008

JON W. DUDAS
*Director of the United States Patent and Trademark Office*